(12) United States Patent
El-Gamal

(10) Patent No.: US 11,390,601 B2
(45) Date of Patent: Jul. 19, 2022

(54) CONFORMATIONALLY-RESTRICTED ANALOGUES OF SORAFENIB AND REGORAFENIB AS SELECTIVE KINASE INHIBITORS FOR CANCER TREATMENT

(71) Applicant: University of Sharjah, Sharjah (AE)

(72) Inventor: Mohammed I El-Gamal, Sharjah (AE)

(73) Assignee: UNIVERSITY OF SHARJAH, Sharjah (AE)

( * ) Notice: Subject to any disclaimer, the term of this patent is extended or adjusted under 35 U.S.C. 154(b) by 0 days.

(21) Appl. No.: 16/945,039

(22) Filed: Jul. 31, 2020

(65) Prior Publication Data
US 2022/0033375 A1 Feb. 3, 2022

(51) Int. Cl.
*C07D 401/04* (2006.01)
*A61P 35/00* (2006.01)

(52) U.S. Cl.
CPC .................. *C07D 401/04* (2013.01)

(58) Field of Classification Search
CPC ............... C07D 401/04; A61P 35/00
See application file for complete search history.

(56) References Cited

U.S. PATENT DOCUMENTS 9,657,012 B2 * 5/2017 Hudson .................. A61P 25/32

OTHER PUBLICATIONS

Golub et al. Science, vol. 286, Oct. 1999, pp. 531-537.*

* cited by examiner

*Primary Examiner* — Samira J Jean-Louis
(74) *Attorney, Agent, or Firm* — Hayes Soloway P.C.

(57) ABSTRACT

Novel conformationally-restricted analogues of sorafenib and regorafenib as selective kinase inhibitors for therapeutic formulations and methods for treating cancer.

14 Claims, 13 Drawing Sheets

Designed target compounds

X = H, F
R = Ar-CO, Ar-NHCO, Ar-SO₂, Ar-NHCS
(Ar = Ph, 3,4-dichlorophenyl, 3-(trifluoromethyl)phenyl, 4-chloro-3-(trifluoromethyl)phenyl, 4-fluoro-3-(trifluoromethyl)phenyl, 3,5-bis(trifluoromethyl)phenyl)

Compound 1f

Sorafenib

| Compound | % of survived cells (mean of duplicate assay ± S.D.) | |
|---|---|---|
| | Hep3B | Huh7 |
| Control | 100% ± 0.11 | 108% ± 0.09% |
| Sorafenib | 33% ± 0.03% | 21% ± 0.01% |
| 1a | 66% ± 0.02% | 74% ± 0.04% |
| 1b | 46% ± 0.02% | 43% ± 0.03% |
| 1c | 58% ± 0.01% | 68% ± 0.04% |
| 1d | 53% ± 0.03% | 40% ± 0.03% |

FIG. 8A

| Structure | | |
|---|---|---|
| 1e (4-F, 3-CF3 phenyl urea indole pyridine carboxamide) | 49% % ± 0.01% | 65% ± 0.05% |
| 1f (3,5-bis-CF3 phenyl urea indole pyridine carboxamide) | 73% ± 0.03% | 30% ± 0.03% |
| 1g (4-morpholino-3-CF3 phenyl urea indole pyridine carboxamide) | 27% ± 0.01% | 28% ± 0.01% |
| 1h (4-(4-methylpiperazinyl)-3-CF3 phenyl urea indole pyridine carboxamide) | 29% ± 0.03% | 20% ± 0.02% |
| 1i (benzamide indole pyridine carboxamide) | 92% ± 0.02% | 105% ± 0.05% |
| 1j (3,4-dichlorobenzamide indole pyridine carboxamide) | 79% ± 0.02% | 61% ± 0.04% |

FIG. 8B

| Compound | | |
|---|---|---|
| 1k | 72% ± 0.03% | 77% ± 0.04% |
| 1l | 59% ± 0.10% | 40% ± 0.03% |
| 1m | 111% ± 0.02% | 77% ± 0.04% |
| 1n | NT | NT |
| 1o | 54 ± 0.01 | 42 ± 0.01 |
| 1p | 93% ± 0.02% | 105% ± 0.06% |

FIG. 8C

| Compound | | |
|---|---|---|
|  1q | 92% ± 0.02% | 94% ± 0.08% |
|  1r | 84% ± 0.03% | 94% ± 0.08% |
|  1s | 92% ± 0.02% | 101% ± 0.07% |
|  1t | NT | NT |
|  1u | 92% ± 0.03% | 121% ± 0.08% |
|  1v | 64% ± 0.02% | 89% ± 0.06% |

| Structure | | |
|---|---|---|
| 1w | 86% ± 0.02 | 109% ± 0.06% |
| 1x | 40% ± 0.02% | 76% ± 0.06% |
| 1y | 55% ± 0.02% | 40% ± 0.02% |

FIG. 8E

| Compound Number | IC$_{50}$ (µM) ± S.D. | |
|---|---|---|
| | Hep3B | Huh7 |
| 1b | 7.94 ± 0.11 | 7.96 ± 0.12 |
| 1d | 12.32 ± 0.11 | 15.36 ± 0.08 |
| 1f | 29.80 ± 0.06 | 5.01 ± 0.12 |
| 1g | 7.38 ± 0.12 | 5.60 ± 0.12 |
| 1h | 8.01 ± 0.15 | 4.31 ± 0.14 |
| 1x | 13.94 ± 0.09 | 21.51 ± 0.09 |
| Sorafenib | 8.62 ± 0.12 | 7.55 ± 0.18 |

FIG. 9

| Kinase | 1h | Sorafenib |
|---|---|---|
| |  | |
| A-RAF | -4% ± 4% | 99.03% ± 0.42% |
| B-RAF (wild-type) | -1% ± 2% | 98.70% ± 0.13% |
| B-RAF (V600E) | 4.5% ± 0.5% | 100% ± 0.08% |
| cKit | 70.5% ± 0.5% | 65.81% ± 0.70% |
| c-RAF | -0.5% ± 1.5% | 99.64% ± 0.15% |
| Flt4/VEGFR3 | 93.5% ± 0.5% | 99.34% ± 0.11% |
| KDR/VEGFR2 | 92.5% ± 1.5% | 99.56% ± 0.09% |
| MEK1 | 11.5% ± 4.5% | 37.74% ± 0.15% |
| PDGFRα | 71.5% ± 1.5% | 99.39% ± 0.35% |
| PDGFRβ | 47.5% ± 2.5% | 99.10% ± 0.09% |

CONFORMATIONALLY-RESTRICTED ANALOGUES OF SORAFENIB AND REGORAFENIB AS SELECTIVE KINASE INHIBITORS FOR CANCER TREATMENT

TECHNICAL FIELD

The present invention relates to novel conformationally-restricted analogues of sorafenib and regorafenib as selective kinase inhibitors for therapeutic formulations and methods for treating cancer.

BACKGROUND

Cancer has become one of the major health challenges that require continuous efforts to develop efficient drugs. It is the second leading cause of death globally after cardiovascular disorders. The World Health Organization (WHO) expects increments of the number of newly discovered cancer cases to become 15 million cases worldwide every year.

Kinases are over-expressed in several diseases such as cancer. Kinase inhibition has been a hotspot approach for treatment of cancer. The more the kinase selectivity, the less the undesirable side effects.

Sorafenib (Nexavar®) and its fluoro analogue, regorafenib (Stivarga®), are multikinase inhibitor diarylurea derivatives that target A-RAF, B-RAF (wild-type), V600E-B-RAF, VEGFR2, VEGFR3, p38α, PDGFRα, PDGFRβ, in addition to C-RAF. They also inhibit basal phosphorylation of ERK (pERK) in numerous cancer cell lines in vitro, including melanoma cell lines, independent of their K-RAS and B-RAF mutational status.

Dysregulated signaling through RAF kinase isoforms has been detected in ~30% of human cancers. Constitutive B-RAF activity can be caused by activating oncogenic mutations, such as B-RAF V600E mutation, which is prevalent in melanomas (63%). C-RAF kinase is an essential growth factor for renal cell carcinoma, breast cancer, and melanoma. C-RAF is also related to poor prognosis in ovarian and androgen-insensitive prostate cancer. Furthermore, C-RAF/MEK dual inhibition has been reported to induce apoptosis in colorectal cancer cell lines such as HCT-116.

Both sorafenib and regorafenib are flexible structures with several conformers, thus this is a potential cause of kinase non-selectivity. The kinase non-selectivity of sorafenib/regorafenib leads to narrow safety margin and high risk of side effects. There is a need for improved kinase selectivity in the treatment of cancers associated with an altered expression of kinases.

SUMMARY OF THE EMBODIMENTS

A study was conducted where more rigid analogues of sorafenib/regorafenib were evaluated in order to minimize the number of conformers of sorafenib/regorafenib, and thereby improve kinase selectivity. In the present study, the antiproliferative effects of analogues of sorafenib/regorafenib on hepatocellular carcinoma cell lines were investigated. Upon testing some compounds against a panel of kinases inhibited by sorafenib and regorafenib, our target compound inhibited only 1-2 of them.

The advantage is the ability of the target compounds to kill cancer cells with high selectivity and less toxicity and side effects. So far, no disadvantages appeared. In case of disadvantages, they can be overcome by modification of the structure to attain better properties. In representative embodiments, the compounds of the present invention contain either a urea linker similar to sorafenib/regorafenib, or amide, thiourea, or sulfonamide. The phenoxy part of the structure has been rigidifled, but not the aryl urea part, because the NH and CO groups of the urea linker are essential for binding with kinases (FIG. 1). In a first aspect of the present disclosure, there is provided a compound according to formula I:

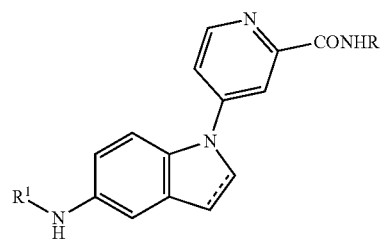

wherein:
R=H, alkyl, aralkyl, aryl, or heteroaryl; The dotted bond can be single or double; $R^1$=-(L)-$R^2$, wherein L is selected from a group consisting of: a covalent bond, —C(O), —C(O)—NH—, —C(S)—NH—, —S(O$_2$)—$R^2$, wherein $R^2$ is:

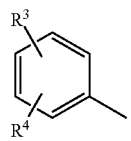

wherein $R^3$ and $R^4$ are independently selected from the group consisting of: halogen, C1-C5 alkyl, C1-C5 alkyl substituted with 1, 2, or 3 halogen atoms, C3-C10 cycloalkyl, morpholino optionally substituted with C1-C5 alkyl, and piperazine substituted with C1-C5 alkyl:

In one embodiment of the present disclosure, there is provided a compound independently selected from the group consisting of:

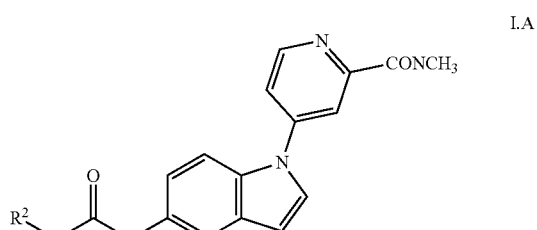

I.A

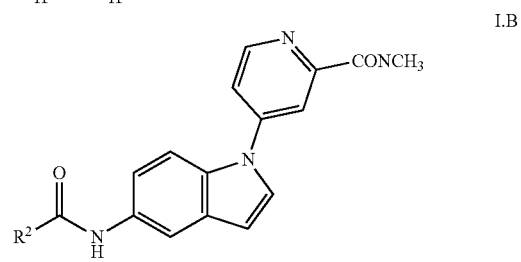

I.B

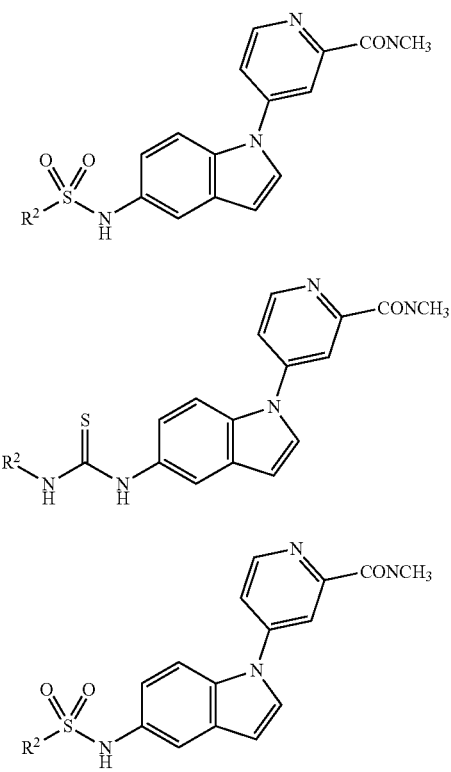
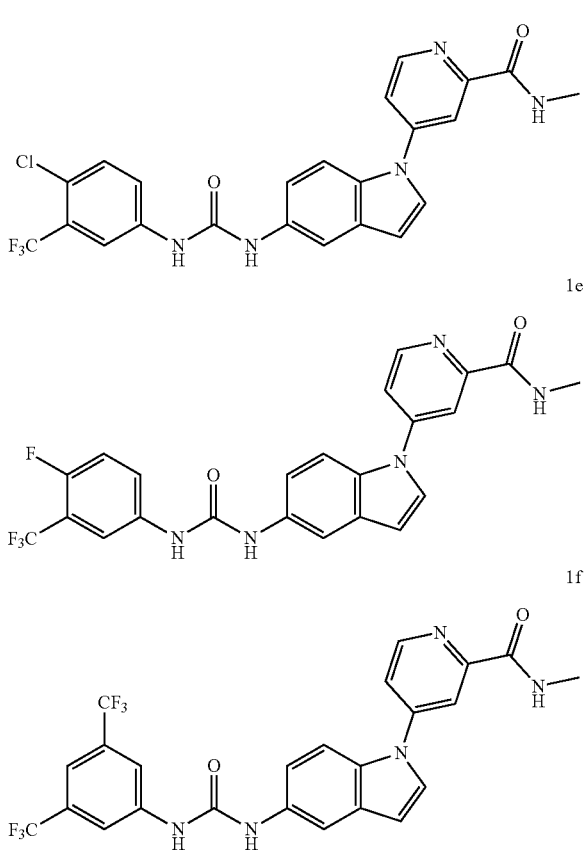
In another embodiment of the present disclosure, there is provided a compound independently selected from a group consisting of:
In a further embodiment of the present disclosure, there is provided a compound independently selected from a group consisting of:
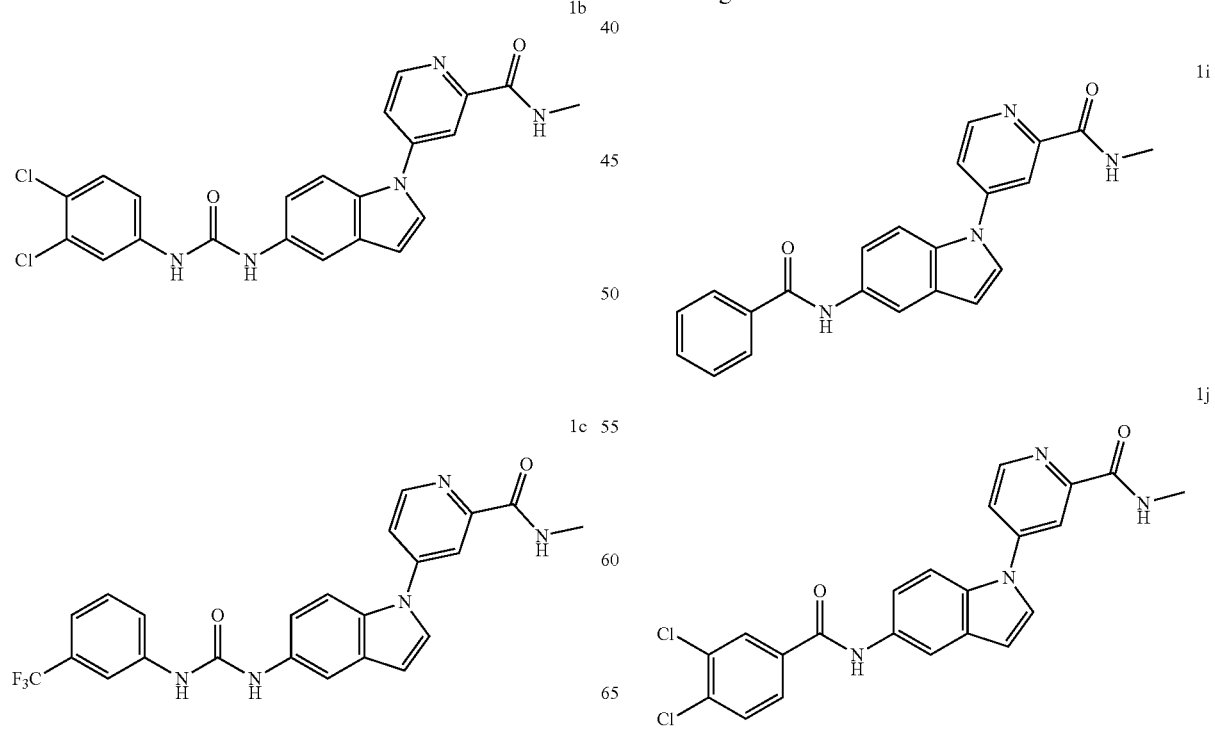

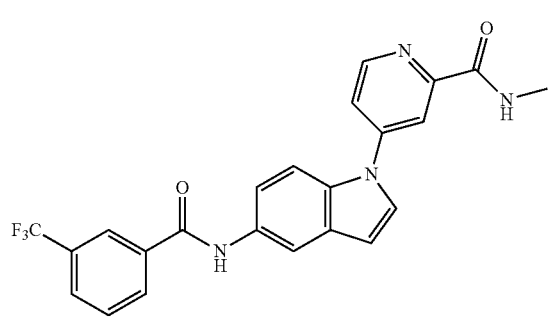
1k
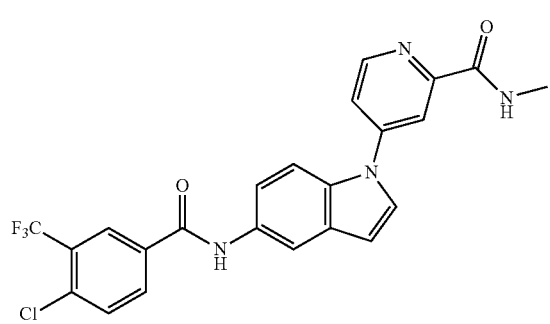
1l
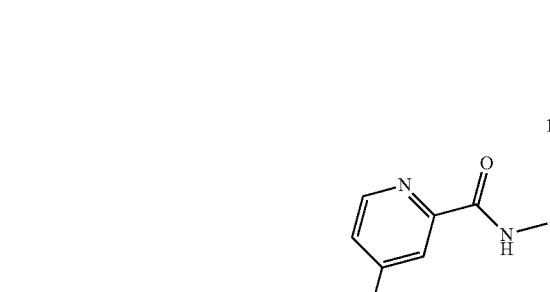
1m
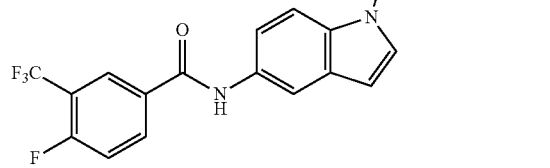
1n
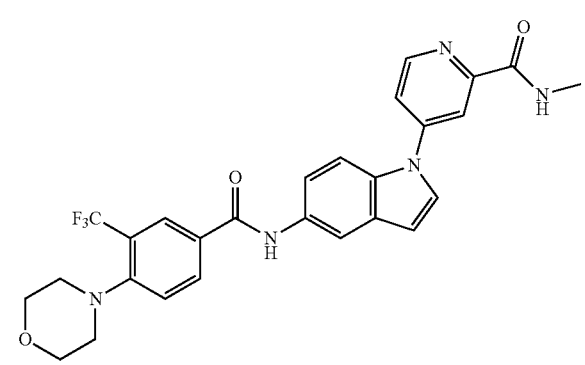
1o
In an additional embodiment of the present disclosure, there is provided a compound independently selected from a group consisting of:
1p
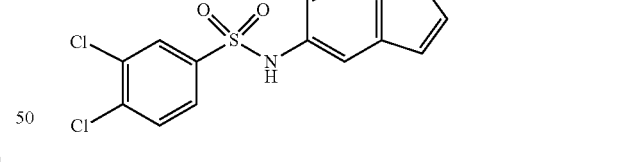
1q
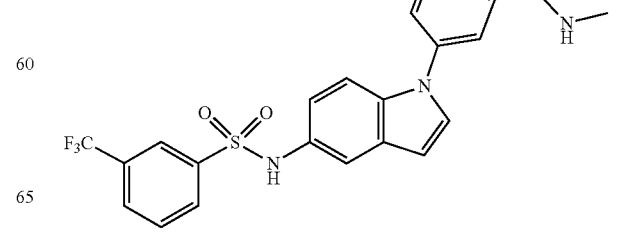
1r

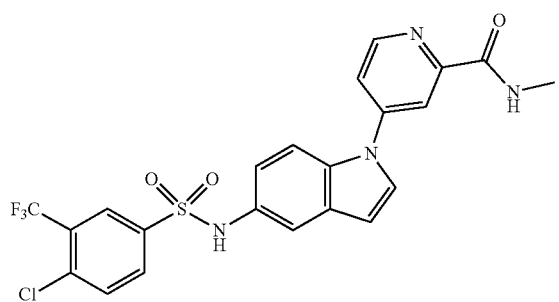
1s
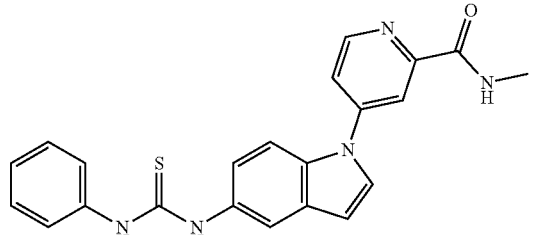
1t
In another embodiment of the present disclosure, there is provided a compound independently selected from a group consisting of:
1u
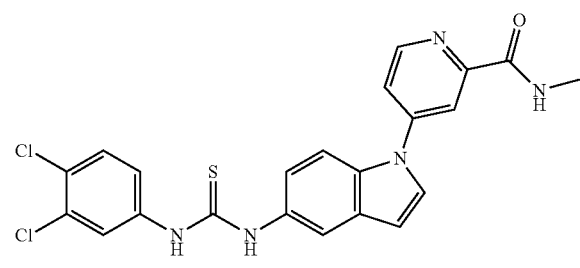
1v
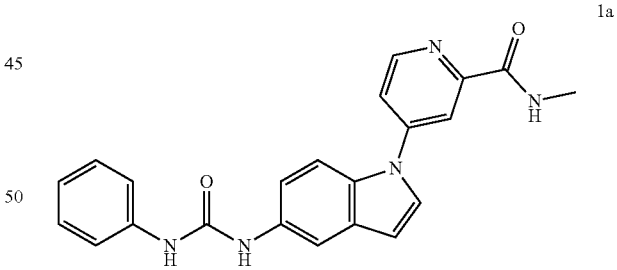
1w
1x
1y
In a preferred embodiment of the present disclosure, there is provided a compound independently selected from a group consisting of:
1a
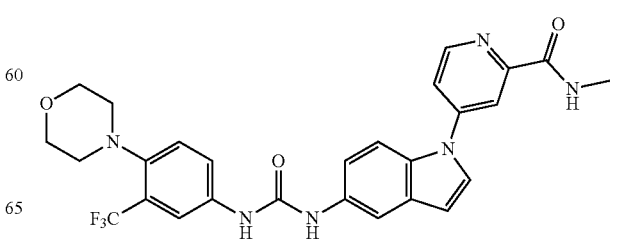
1g

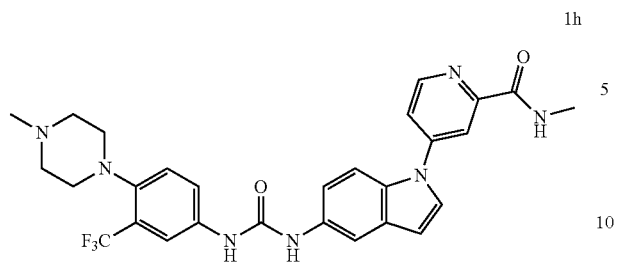
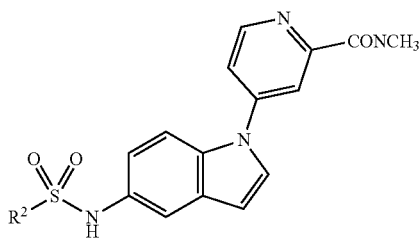

In a second aspect of the present disclosure, there is provided a method of treating a subject afflicted by a cancer associated with an altered expression of one or more kinases, by administering to the subject a therapeutically effective amount of compound I, or a pharmaceutically acceptable salt thereof, and one or more pharmaceutical excipients.

The above-mentioned treatment, wherein the compound is independently selected from the group consisting of:

In a first embodiment of the above-mentioned treatment, $R^2$ can be alkyl, cycloalkyl, or (substituted) aryl. The compound is independently selected from the group consisting of:

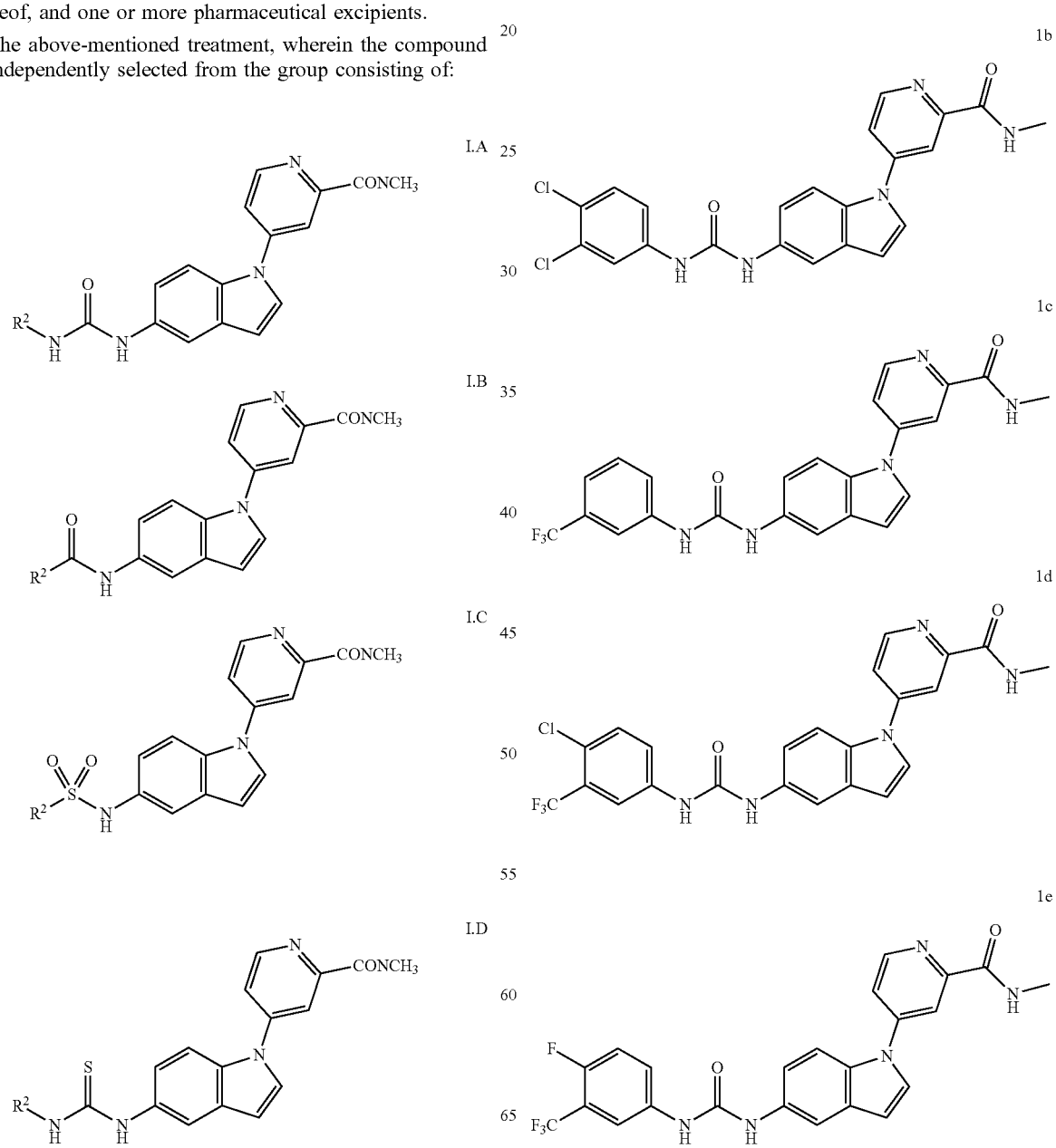

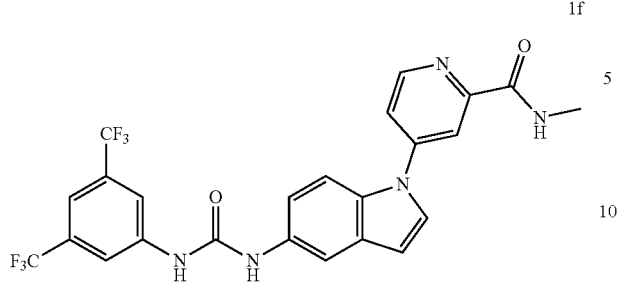
In a second embodiment of the above-mentioned treatment, the compound is independently selected from the group consisting of:
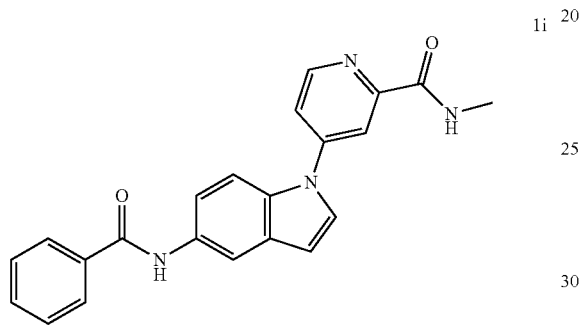
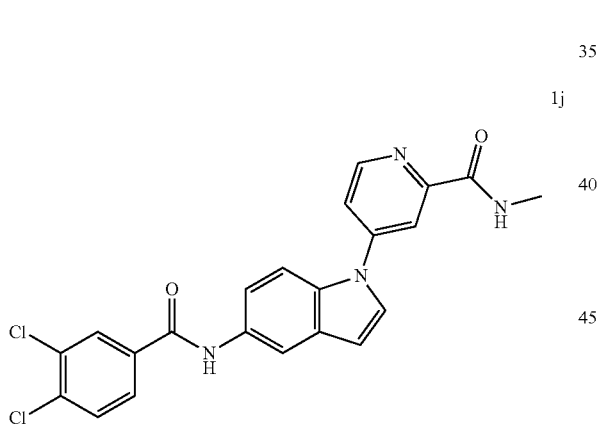
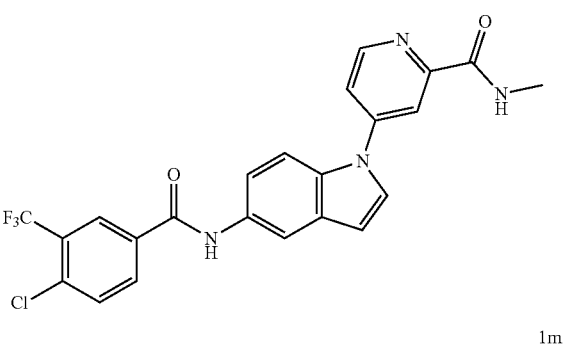
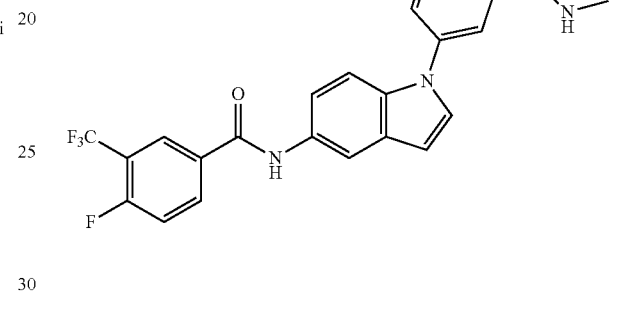
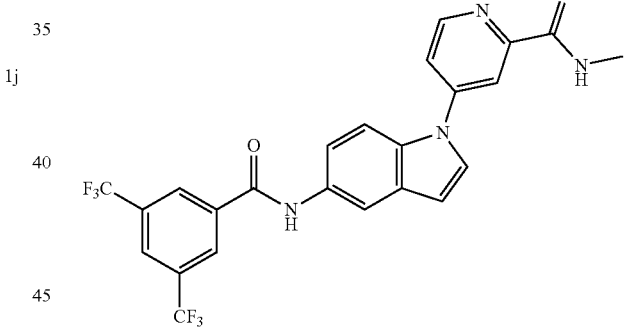
In a third embodiment of the above-mentioned treatment, the compound is independently selected from the group consisting of:
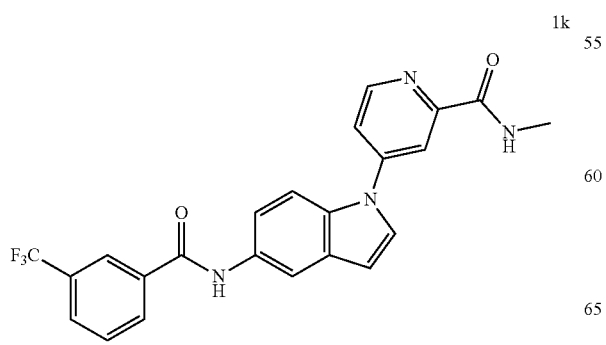
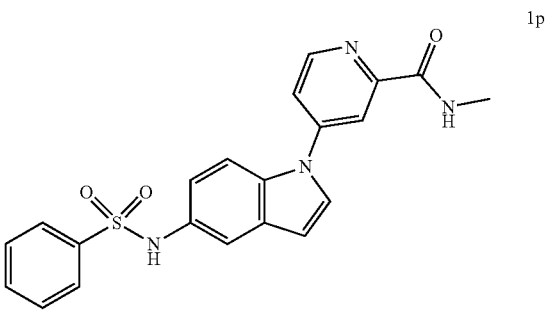

-continued

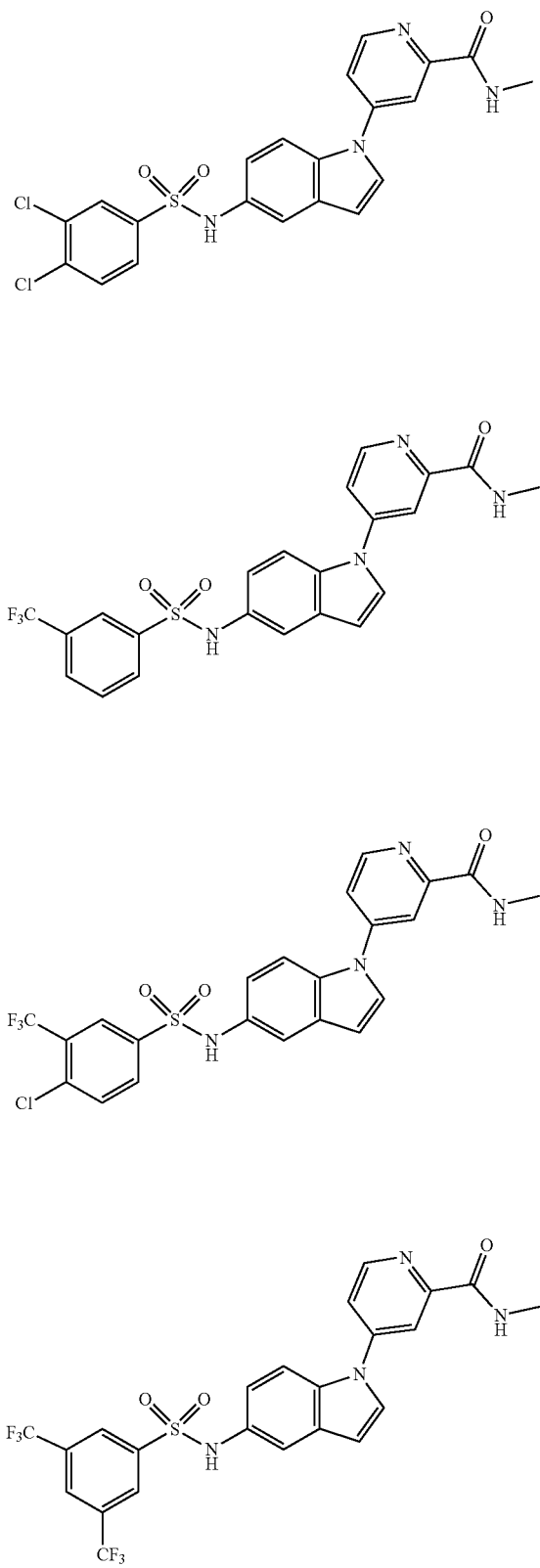

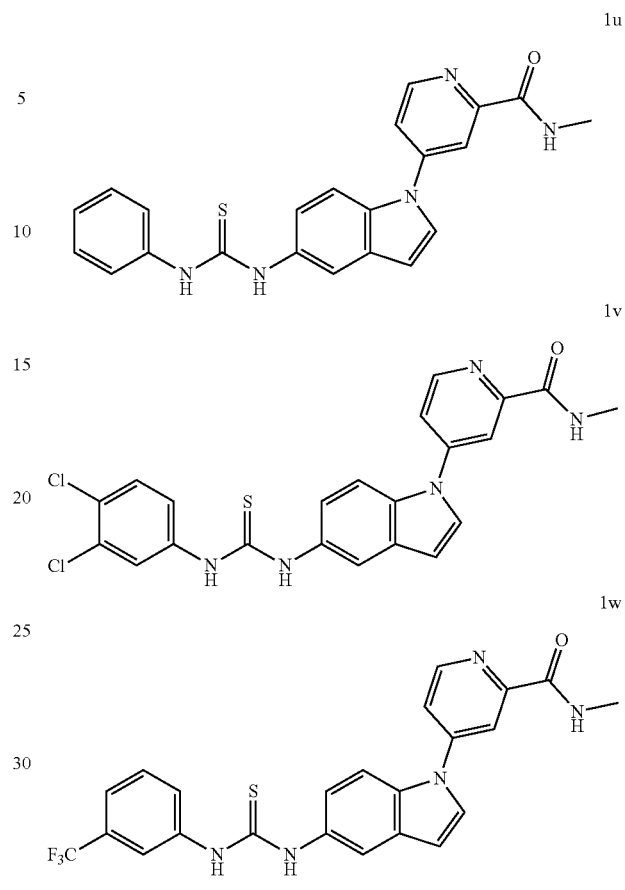

In a most preferred embodiment of the above mentioned treatment, the compound is independently selected from the group consisting of:

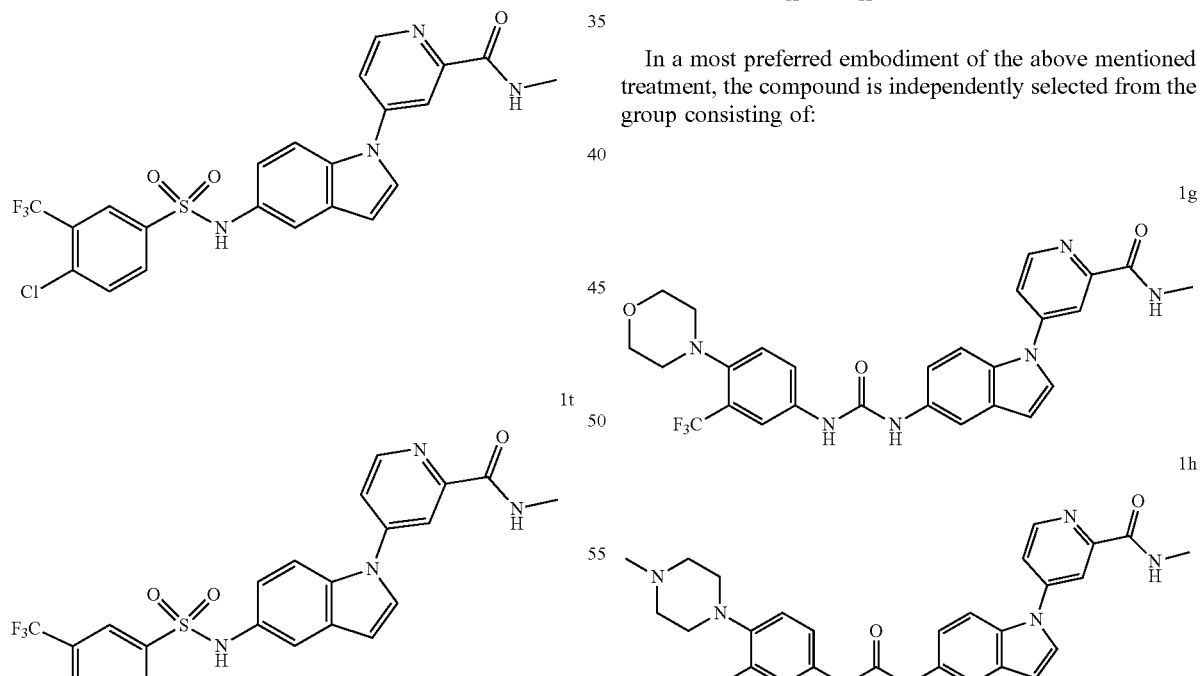

In a preferred embodiment of the above-mentioned treatment, the compound is independently selected from the group consisting of:

Compositions featuring the above mentioned compounds may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations may conveniently be presented in unit dosage form and may be prepared by any methods well known in the art of pharmacy. The amount of compound which can be combined with a carrier material to produce a single dosage form will vary depending upon the subject being treated, the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

In certain embodiments, a formulation of the compound includes an excipient selected from the group consisting of cyclodextrins, liposomes, micelle forming agents, e.g., bile acids, and polymeric carriers, e.g., polyesters and polyanhydrides; and an active ingredient that may be the compound and/or one of its pharmaceutically acceptable derivatives. In certain embodiments, an aforementioned formulation renders orally bioavailable a compound or its derivative.

Methods of preparing these formulations or compositions include the step of bringing into association the compound with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

Liquid dosage forms for oral administration of the compound include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A formulation of the compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also include buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The tablets, and other solid dosage forms of the formulation of the compound, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the compound for rectal or vaginal administration may be presented as a suppository, which may be prepared by the compound with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of the compound include powders, sprays, ointments, pastes, creams, lotions, gels, solutions, patches and inhalants. The extract may be mixed under sterile conditions with a pharmaceutically-acceptable carrier, and with any preservatives, buffers, or propellants which may be required. The ointments, pastes, creams and gels may contain, in addition to an extract, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an extract, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compound to the body. Such dosage forms can be made by dissolving or dispersing an extract in the proper medium. Absorption enhancers can also be used to increase the flux of the extract or dispersing the extract in a polymer matrix or gel.

Pharmaceutical compositions suitable for parenteral administration include one or more components of the compound in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compound may be formulated into pharmaceutically-acceptable dosage forms by conventional methods known to those of skill in the art. The compound may be formulated for administration in any convenient way for use in human or veterinary medicine, by analogy with other pharmaceuticals.

In certain embodiments, the above-described pharmaceutical compositions include the compound, a chemotherapeutic agent, and optionally a pharmaceutically acceptable carrier. Alternatively, the terms "chemotherapeutic agent" or "therapeutic agent" include, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and *vinca* alkaloid natural antineoplastics, such as vinblastine and vincristine.

Methods of Cancer Treatment

The above compound compositions may be used in novel therapeutic methods of treatment in cancer patients. The methods include administering to a subject an effective amount of a pharmaceutical compound composition. In representative embodiments, the subject suffers from a liver cancer. In specific embodiments, the type of liver cancer is a hepatocellular carcinoma (HCC), fibrolamellar HCC, cholangiocarcinoma, angiosarcoma, or liver cancer.

The above invention can be used to treat any cancer irrespective of the type or cause of the cancer, and irrespective of the genetic lesions associated with it, including, hut not limited to cancer, pre-cancerous cells, tumors, neoplasms, and non-malignant tumors can also be treated. Cancers that can be treated include, e.g., cancers which are primary; which arise from a primary tumor at a secondary metastatic site; which have been treated by surgery (e.g., entirely removed, surgical resection, etc); which have been treated by chemotherapy, radiation, radiofrequency ablation, and/or any other adjunct to drug therapy; which have acquired drug-resistance; which are refractory to a chemotherapeutic agent.

The phrase "effective amount" indicates the amount of the compound which is effective to treat any symptom or aspect of the cancer. Effective amounts can be determined routinely. Further guidance on dosages and administration regimens is provided below.

The term "treatment" is used conventionally, e.g., the management or care of a subject for the purpose of combating, alleviating, reducing, relieving, improving, etc., one or more of the symptoms associated with a cancer, including all cancers mentioned herein and in Table 1.

Administering effective amounts of the compound can treat one or more aspects of the cancer disease, including, but not limited to, causing tumor regression; causing cell death; causing apoptosis; causing necrosis; inhibiting cell proliferation; inhibiting tumor growth; inhibiting tumor metastasis, inhibiting tumor migration; inhibiting tumor invasion; reducing disease progression; stabilizing the disease; reducing or inhibiting angiogenesis; prolonging patient survival, enhancing patient's quality of life; reducing adverse symptoms associated with cancer; and reducing the frequency, severity, intensity, and/or duration of any of the aforementioned aspects.

The term "subject" in accordance with the present invention, includes, e.g., mammals, such as dogs, cats, horses, rats, mice, monkeys, and humans.

In other embodiments, types of cancer which can be treated in accordance with present invention include, but are not limited to: Ceil Adult Acute Lymphoblastic Leukemia; Elastic Phase Chronic Myelogenous Leukemia; Bone Metastases; Brain Tumor; Breast Cancer; Cancer; Central Nervous System Cancer; Childhood Acute Lymphoblastic Leukemia, Childhood Acute Lymphoblastic Leukemia in Remission; Childhood Central Nervous System Germ Cell Tumor; Childhood. Chronic Myelogenous Leukemia; Childhood Soft Tissue Sarcoma; Chordoma; Chronic Eosinophilic Leukemia (CEL); Chronic Idiopathic Myelofibrosis; Chronic Myelogenous Leukemia; Chronic Myeloid Leukemia; Chronic Myelomonocytic Leukemia; Chronic Phase Chronic Myelogenous Leukemia; Colon Cancer; Colorectal Cancer; Dermatofibrosarcoma; Dermatofibrosarcoma Protuberans (DFSP); Desmoid Tumor, Eosinophilia, Epidemic Kaposi's Sarcoma; Essential Thrombocythemia; Ewing's Family of Tumors; Extensive Stage Small Cell Lung Cancer; Fallopian Tube Cancer; Familiar Hypereosinophilia; Fibrosarcoma; Gastric Adenocarcinoma; Gastrointestinal Neoplasm; Gastrointestinal Stromal Tumor; Glioblastoma; Glioma; Gliosarcoma; Grade I Meningioma; Grade II Meningioma; Grade III Meningioma; Hematopoietic and Lymphoid Cancer, High-Grade Childhood Cerebral Astrocytoma; Hypereosinophilic Syndrome; Idiopathic Pulmonary Fibrosis; L1 Adult Acute Lymphoblastic Leukemia; L2 Adult Acute Lymphoblastic Leukemia; Leukemia, Lymphocytic, Acute L2; Leukemia, Myeloid, Chronic; Leukemia, Myeloid, Chronic Phase; Liver Dysfunction and Neoplasm; Lung Disease; Lymphoid Blastic Phase of Chronic Myeloid Leukemia, Male Breast Cancer; Malignant Fibrous Histiocytoma; Mastocytosis; Meningeal Hemangiopericytoma; Meningioma; Meningioma; Meningioma; Metastatic Cancer; Metastatic Solid Tumors; Myelofibrosis, Myeloid Leukemia, Chronic; Myeloid Leukemia, Chronic Accelerated-Phase, Myeloid Leukemia, Chronic, Chronic-Phase; Myeloid Metaplasia; Myeloproliferative Disorder (MPD) with Eosinophilia; Neuroblastoma; Non-T, Non-B Childhood Acute Lymphoblastic Leukemia; Oligodendroglioma; Osteosarcoma; Ovarian Germ Cell Tumor; Ovarian Low Malignant Potential Tumor, Ovarian Neoplasms, Pancreatic Cancer, Pelvic Neoplasms; Peritoneal Cavity Cancer, Peritoneal Neoplasms; Philadelphia Chromosome Positive Chronic Myelogenous Leukemia; Philadelphia Positive Acute Lymphoblastic Leukemia; Philadelphia Positive Chronic Myeloid Leukemia in Myeloid Blast Crisis; Polycythemia Vera; Pulmonary Fibrosis; Recurrent Adult Brain Tumor; Recurrent Adult Soft Tissue Sarcoma; Recurrent Breast Cancer; Recurrent Colon Cancer; Recurrent Esophageal Cancer; Recurrent Gastric Cancer; Recurrent Glioblastoma Multiforme (GBM); Recurrent Kaposi's Sarcoma; Recurrent Melanoma; Recurrent Merkel Cell Carcinoma; Recurrent Ovarian Epithelial Cancer; Recurrent Pancreatic Cancer; Recurrent Prostate Cancer, Recurrent Rectal Cancer, Recurrent Salivary Gland Cancer; Recurrent Small Cell Lung Cancer; Recurrent Tumors of the Ewing's Family; Recurrent Uterine Sarcoma; Relapsing Chronic Myelogenous Leukemia; Rheumatoid Arthritis; Salivary Gland Adenoid Cystic Carcinoma; Sarcoma; Small Cell Lung Cancer; Stage U Melanoma; Stage II Merkel Cell Carcinoma; Stage III Adult Soft Tissue Sarcoma; Stage III Esophageal Cancer; Stage III Merkel Cell Carcinoma; Stage ill Ovarian Epithelial Cancer; Stage III Pancreatic Cancer; Stage III Salivary Gland Cancer; Stage IUB Breast Cancer; Stage UIC Breast Cancer; Stage IV Adult Soft Tissue Sarcoma; Stage IV Breast Cancer; Stage IV Colon Cancer; Stage IV Esophageal Cancer; Stage IV Gastric Cancer; Stage IV Melanoma; Stage IV Ovarian Epithelial Cancer; Stage IV Prostate Cancer; Stage IV Rectal Cancer; Stage IV Salivary Gland Cancer; Stage IVA Pancreatic Cancer; Stage IVB Pancreatic Cancer; Systemic Mastocytosis; T-CeII Childhood Acute Lymphoblastic Leukemia; Testicular Cancer; Thyroid Cancer; Unresectable or Metastatic Malignant Gastrointestinal Stromal Tumor (GIST); Unspecified Adult Solid Tumor; Untreated Childhood Brain Stem Glioma; Uterine Carcinosarcoma, and Uterine Sarcoma. [0014] Diseases which can be treated in accordance with present invention include, e.g., diseases which are treated with gefitinib, such as, but not limited to: Adenocarcinoma of the Colon; Adenocarcinoma of the Esophagus, Adenocarcinoma of the Lung, Adenocarcinoma of the Prostate; Adenocarcinoma of the Rectum; Advanced Adult Primary Liver Cancer; Advanced Non-Nasopharyngeal Head and Neck Carcinoma; Anaplastic Astrocytoma; Anaplastic Oligodendroglioma; Anaplastic Thyroid Cancer; Bladder Cancer; Brain Tumor; Breast Cancer; Breast Cancer in Situ; Breast Neoplasms; Bronchoalveolar Cell Lung Cancer; Cancer of the Fallopian Tube; Carcinoma, Squamous Cell; Cervix Neoplasms; Colon Cancer; Colorectal Cancer; Epithelial Mesothelioma; Esophageal Cancer, Esophagogastric Cancer; Follicular Thyroid Cancer; Gastric Cancer; Gastrinoma: Gastrointestinal Carcinoid; Giant Cell Glioblastoma; Glioblastoma; Glioblastoma Multiforme, Head and Neck Cancer; Hepatocellular Carcinoma; Hypopharyngeal Cancer; Inoperable Locally Advanced Squamous Cell Carcinoma of Head and Neck; Insulinoma; Intraductal Breast Carcinoma; Islet Cell Carcinoma; Large Cell Lung Cancer, Laryngeal Cancer; Lip and Oral Cavity Cancer, Lip Cancer; Liver Cancer; Lung Adenocarcinoma With Bronchiole-Alveolar Feature; Lung Cancer; Male Breast Cancer; Medullary Thyroid Cancer; Meningeal Tumors; Metastatic Colorectal Cancer; Metastatic Gastrointestinal Carcinoid Tumor; Metastatic Pancreatic Carcinoma; Mixed Gliomas; Myelogenous Leukemia, Acute; Nasopharyngeal Carcinoma: Neuroblastoma, Non-Metastatic (T2-T4, N0-N3, MO; Stages II and III) and Histologically-Confirmed Intestinal GC; Non-Metastatic Prostate Cancer; Nonresectable Adrenocortical Carcinoma; Non-Small Cell Lung Cancer; Nose Cancer; Oligodendroglial Tumors; Oral Cancer: Oropharyngeal Cancer, Osteosarcoma, Ovarian Cancer; Ovarian Neoplasms; Pancreatic Cancer; Papillary Thyroid Cancer; Peritoneal Carcinoma; Pharynx Cancer, Pneumonic-Type Adenocarcinoma (P-ADC); Primary Hepatocellular Carcinoma; Prostate Cancer; Rectal Cancer: Recurrent Adult Primary Liver Cancer; Recurrent Breast Cancer; Recurrent Colon Cancer; Recurrent Endometrial Cancer, Recurrent Esophageal Cancer; Recurrent Glioblastoma; Recurrent Rectal Cancer; Recurrent Skin Cancer, Refractory Germ Cell Tumors Expressing EGRF; Renal Cell Cancer; Rhabdomyosarcomas; Sarcomatous Mesothelioma; Skin Cancer; Soft Tissue Sarcoma; Squamous Cell Carcinoma of the Esophagus; Squamous Cell Carcinoma of the Head and Neck; Squamous Cell Carcinoma of the Skin; Squamous Cell Lung Cancer; Stage IP Esophageal Cancer; Stage III Esophageal Cancer, Synovial Sarcoma; Thorax and Respiratory Cancer; Throat Cancer; Thyroid Cancer; Transitional Cell Cancer of the Renal Pelvis and Ureter; Transitional Cell Carcinoma of the Bladder, Tubal Carcinoma; Unspecified Childhood Solid Tumor, Untreated Childhood Brain Stem Glioma; Urethral Cancer.

As anticipated above, the compound may be administered by any appropriate route, for example orally, parenterally, topically, or rectally. It will be appreciated that the preferred route may vary with, for example, the condition of the recipient of the compound and the cancer to be treated. In certain embodiments, the extract may be especially suitable for the preparation of pharmaceuticals for intravenous administration, such as intravenous injection or infusion, provided that it does not contain components with serum-precipitating and/or haemagglutinating properties which disturb such an application. The extract may therefore be provided in the form of ampoule preparations which are directed to intravenous administration. In still other embodiments, the method comprises systemic administration of a subject composition to a subject.

Also provided are methods of treating cancer, for example liver cancer, which include administering the compound in conjunction with a chemotherapeutic agent to a subject. Conjunctive therapy includes sequential, simultaneous and separate, or co-administration of the compound and the chemotherapeutic agent in a way that the therapeutic effect of the chemotherapeutic agent is not entirely disappeared when the compound is administered. In certain embodiments, compound and the chemotherapeutic agent may be compounded together in the same unitary pharmaceutical composition including both entities. Alternatively, the combination of compound and chemotherapeutic agent may be administered separately in separate pharmaceutical compositions, each including one of the compound and chemotherapeutic agent in a sequential manner wherein, for example, the compound or the chemotherapeutic agent is administered first and the other second.

Exemplary doses of the compound in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of the compound will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose is in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The combined use of the compound and other chemotherapeutic agents may reduce the required dosage for any individual component because the onset and duration of effect of the different components may be complementary. In such combination therapies, the different active agents may be delivered together or separately, and simultaneously or at different times within the day.

The data obtained from cell culture assays and animal studies may be used in formulating a range of dosage for use in humans. For example, effective dosages achieved in one animal species may be extrapolated for use in another animal, including humans, as illustrated in the conversion table of FIG. 9 where human equivalent dose (FLED) dosage factors based on body surface area of other species are reported. [69], The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For the compound or combinations of the compound and other chemotherapeutic agents, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

In a third aspect of the present disclosure, there is provided a kit for treating a subject afflicted by a cancer associated with an altered expression of one or more kinases, the kit comprising the compound I or a pharmaceutically acceptable salt thereof, and one or more pharmaceutical excipients.

In a preferred embodiment of the above-mentioned kit, the compound is independently selected from the group consisting of:

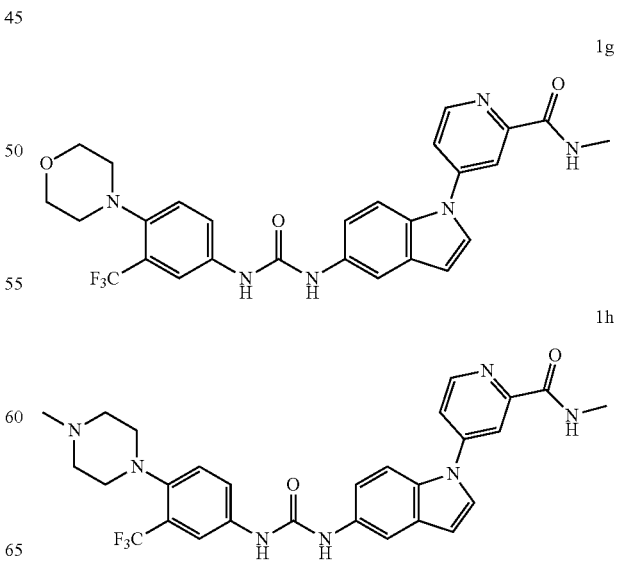

The present invention provides kits for novel therapeutic methods in cancer patients. For example, a kit may include one or more pharmaceutical compositions of the compound as described above. The compositions may be pharmaceutical compositions comprising a pharmaceutically acceptable excipient. In other embodiments involving kits, this invention provides a kit including the compound, optionally a chemotherapeutic agent, and optionally instructions for their use in the treatment of cancer. In still other embodiments, the invention provides a kit comprising one more pharmaceutical compositions and one or more devices for accomplishing administration of such compositions. For example, a subject kit may comprise a pharmaceutical composition and catheter for accomplishing direct intraarterial injection of the composition into a cancer. In an embodiment, the device is an intraarterial catheter. Such kits may have a variety of uses, including, for example, therapy, diagnosis, and other applications.

BRIEF DESCRIPTION OF THE FIGURES

The invention can be better understood with reference to the following figures and description.

FIG. 8A-FIG. 8E illustrate the structures of the target compounds 1a-y and their preliminary antiproliferative activity at 10 μM concentration against Hep3B and Huh7 hepatocellular carcinoma cell lines.

FIG. 9 illustrates $IC_{50}$ results against Hep3B and Huh7 cell lines of compounds 1b, 1d, 1f-h, 1x, and sorafenib.

DEFINITIONS

Figure 1:
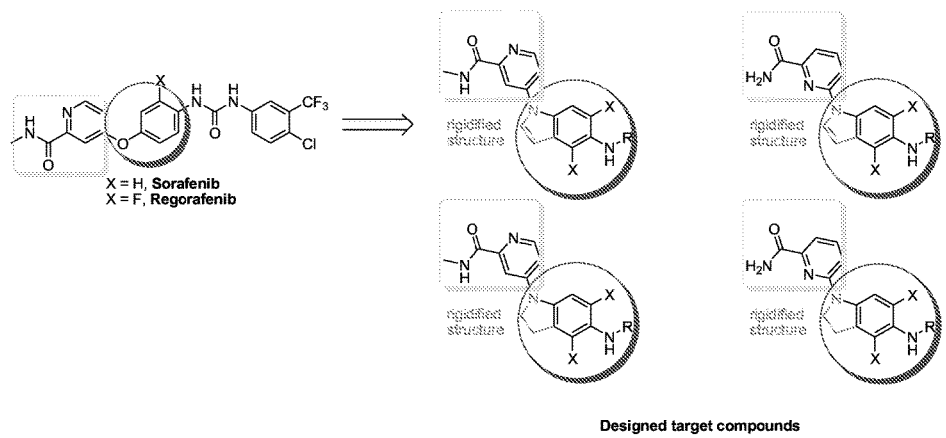
FIG. 1 illustrates the structures of sorafenib and regorafenib, and the designed target indole- and indoline-based compounds.
Figure 2:
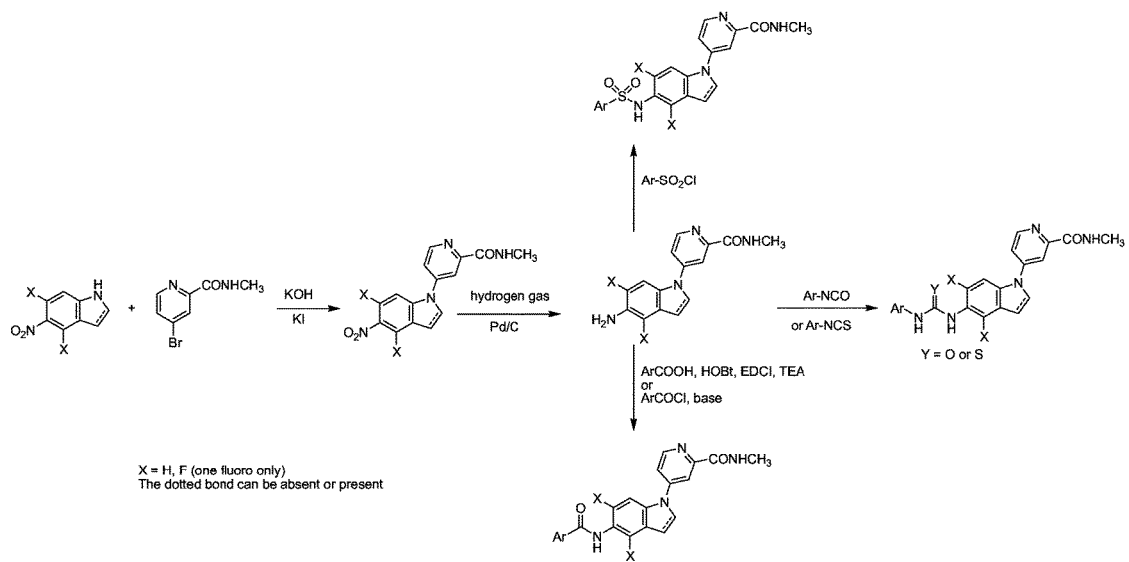
FIG. 2 illustrates the synthesis of the target indole- and indoline-based diarylureas, diarylamides, di aryl thioureas, and diarylsulfonamides.
Figure 3A:
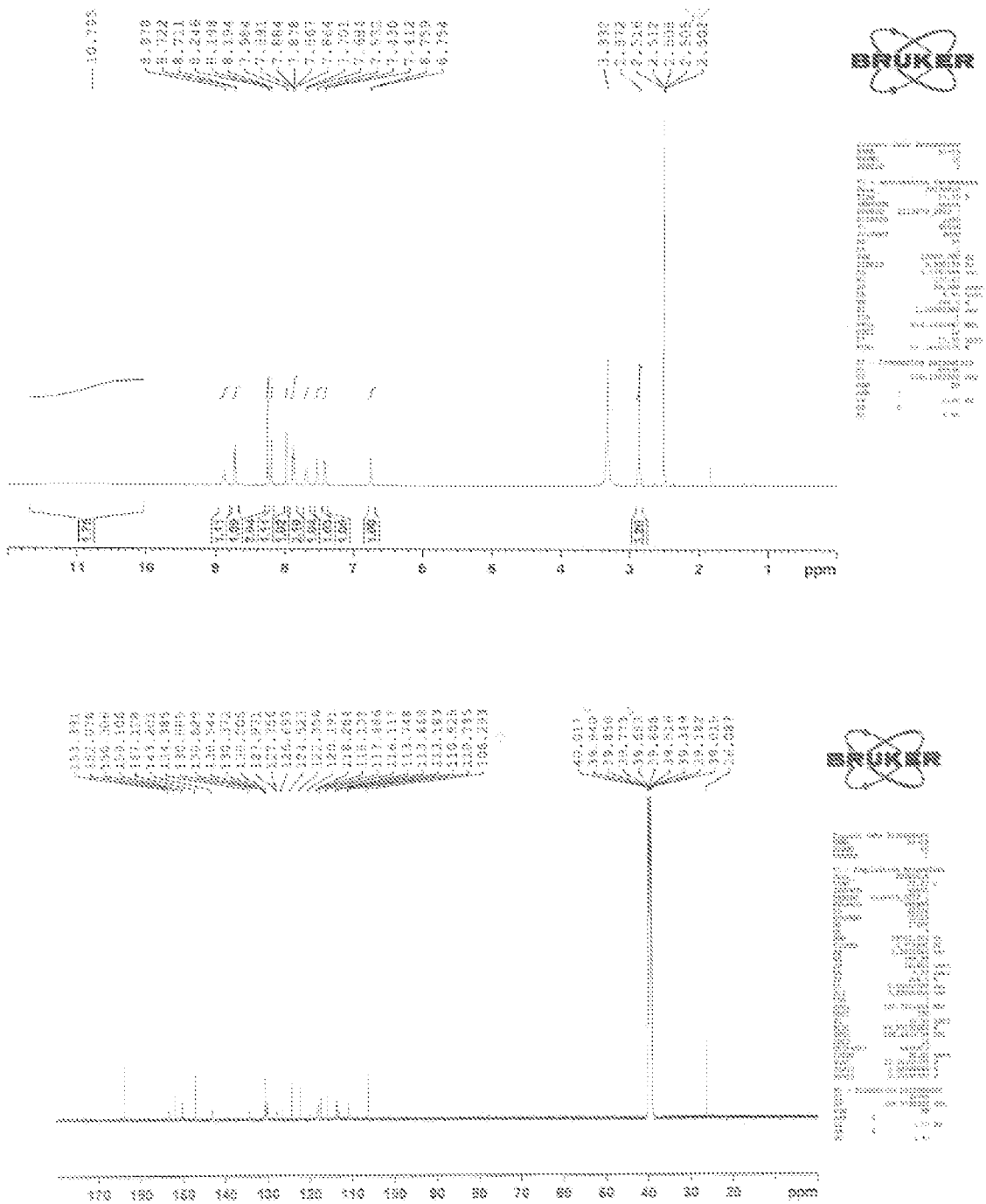
FIG. 3A and FIG. 3B illustrate the analysis charts of the synthesized target compound 1f.
Figure 3B:
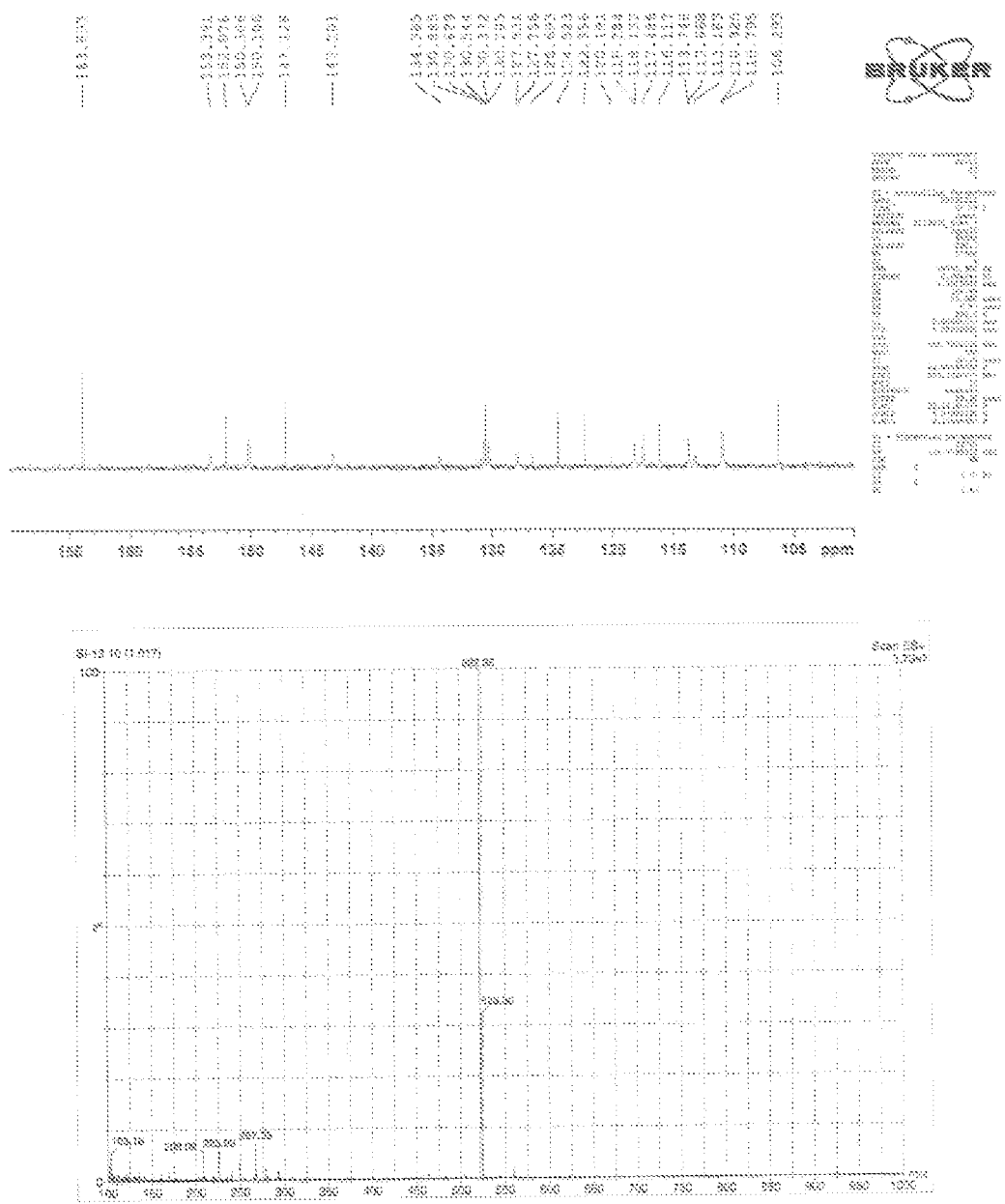
Figure 3B:
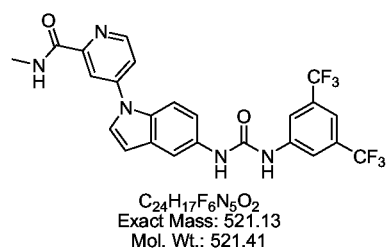
Figure 4:
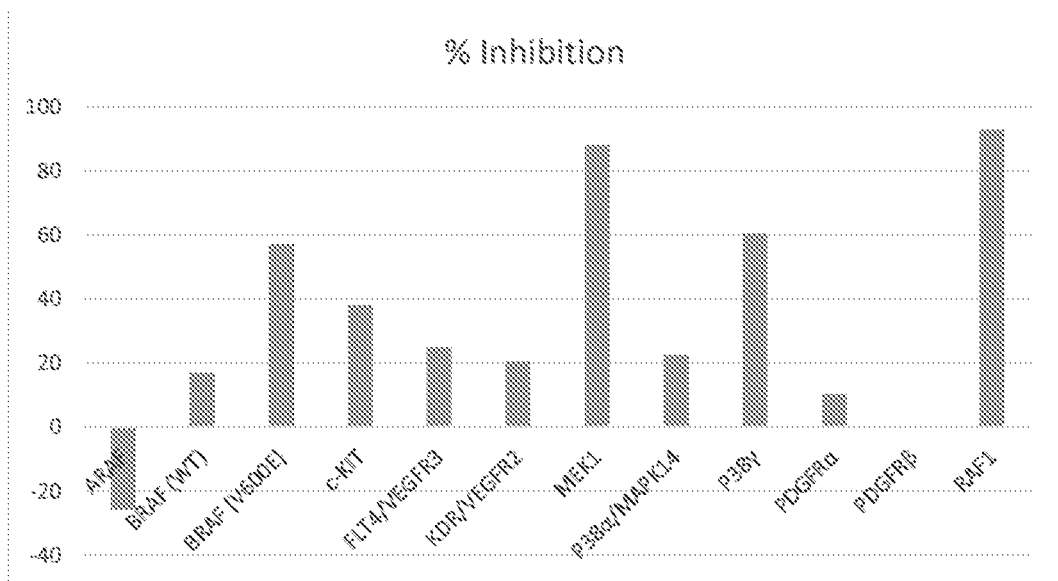
FIG. 4 illustrates the percentage of inhibition of a target compound (10 μM) against a 12-kinase panel.
Figure 5:
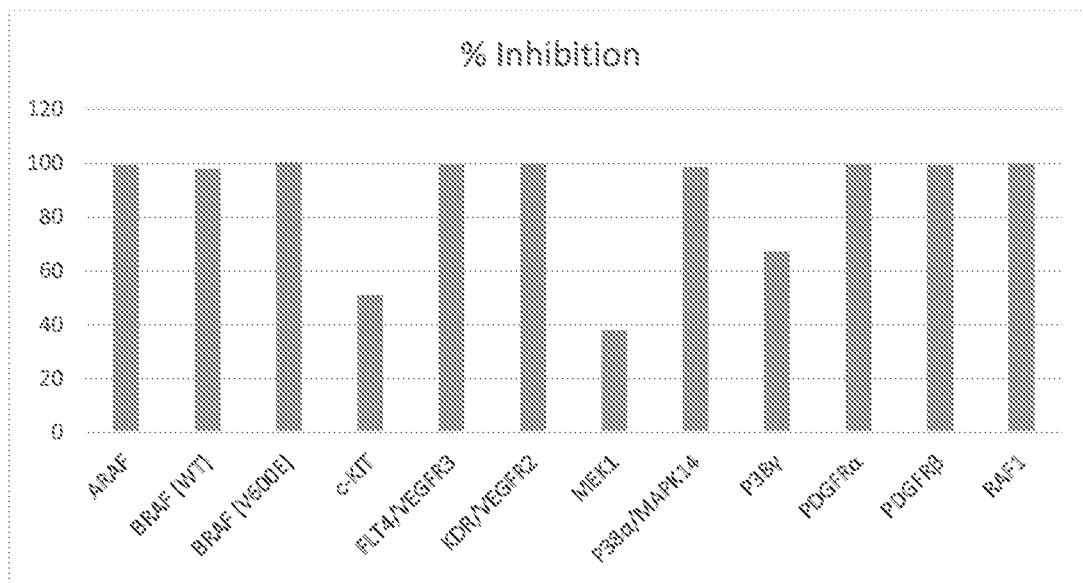
FIG. 5 illustrates the percentage of inhibition of sorafenib (10 μM) against a 12-kinase panel.
Figure 6:
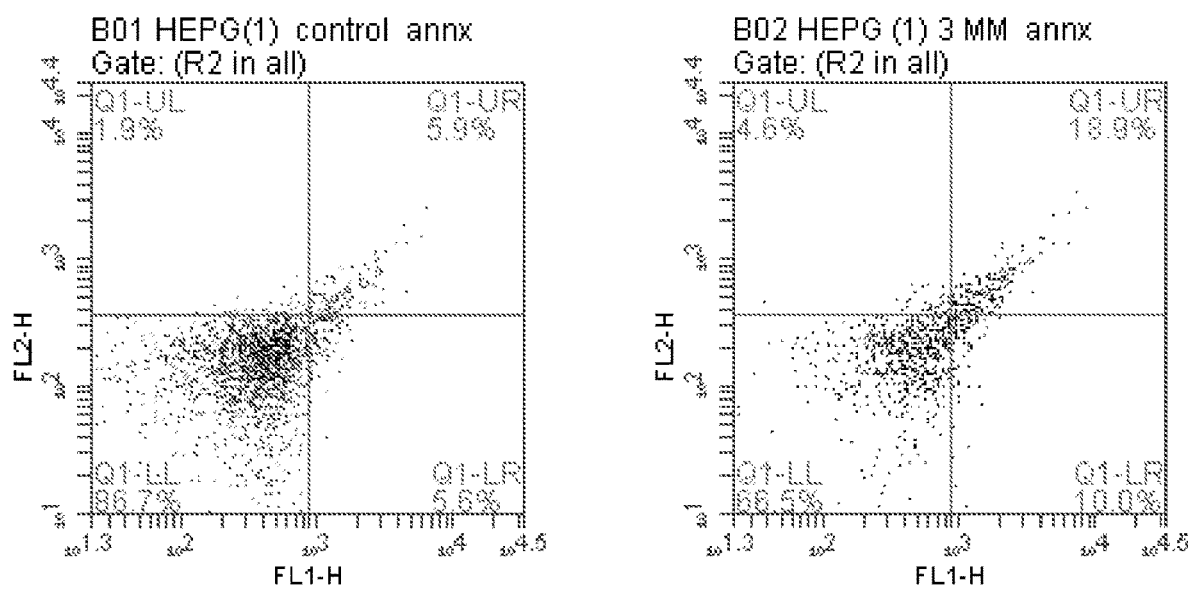
FIG. 6 illustrates induction of apoptosis and/or necrosis in HepG2 cell line by flow cytometry. The $IC_{50}$ value against HepG2 hepatocellular carcinoma cell line is 1.95 μM, 3.7 times more potent than sorafenib The compound induced apoptosis and necrosis at 3 μM concentration.
Figure 7:
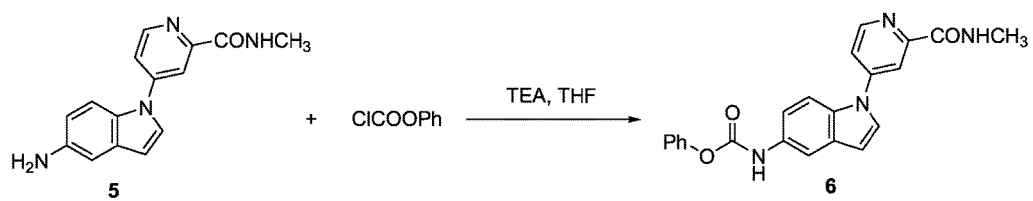
FIG. 7 illustrates the synthesis of the target compounds 1a, 1g, and 1h.
Figure 7:
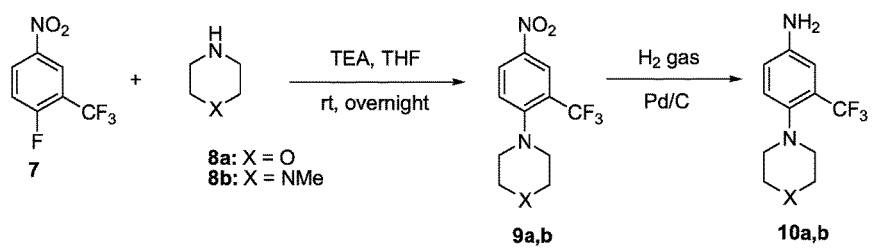
Figure 7:
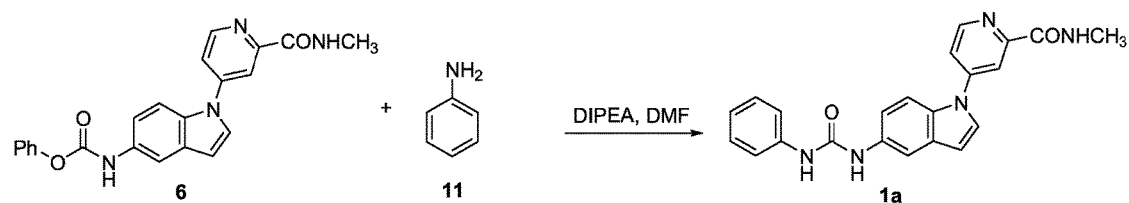
Figure 7:
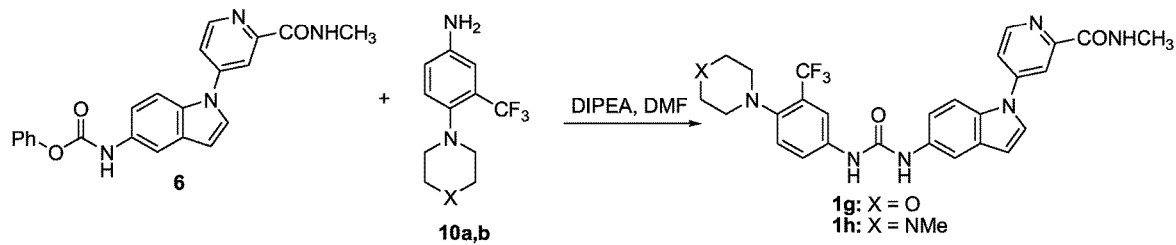
Figure 8D:
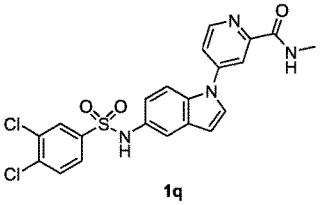
Figure 8D:
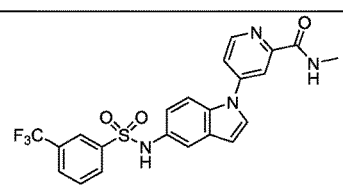
Figure 8D:
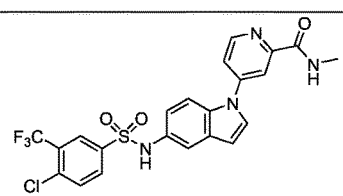
Figure 8D:
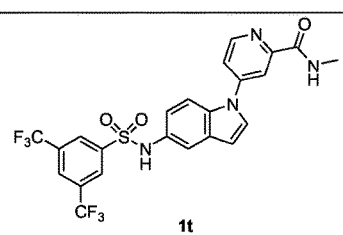
Figure 8D:
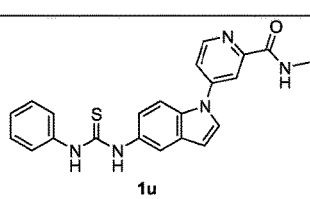
Figure 8D:
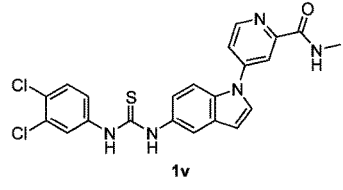
Figure 10:
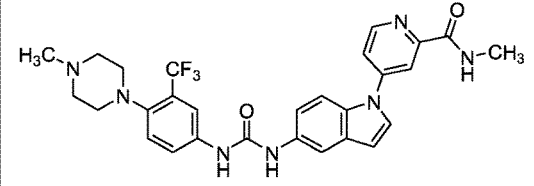
FIG. 10 One-dose kinase results of compound 1h & Sorafenib (% inhibition at 10 μM concentration). The results are expressed as means of duplicate assay ±S.E.M.

As used in this description and the accompanying claims, the following terms shall have the meanings indicated, unless the context otherwise requires:

As used herein, "treatment" is understood to refer to the administration of a drug or drugs to a patient suffering from cancer.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Synthesis of the Intermediate and Target Compounds

Synthesis of N-methyl-4-bromopicolinamide (3)

4-Bromopicolinc acid (20 g, 99.5 mmol) was dissolved in DCM (200 mL) and DMF (4 mL, 51.6 mmol) was added to the stirred solution as a catalyst. Thenceforth, thionyl chloride (17.9 mL, 247.7 mmol) was added in a dropwise manner over a period of 20 minutes to the stirred solution at 0-5° C., followed by refluxing the mixture for 24 hours. Once the completion of the reaction was confirmed, the mixture was concentrated on rotary evaporator. The resulting crude compound was then dissolved in THF (100 mL). The mixture was then added to 40% methylamine solution (100 mL) gradually at 0-5° C. and was left to stir for 4 hours at room temperature. Upon completion of the reaction, the mixture was again dried on rotary evaporator. The concentrated mixture was then extracted with ethyl acetate (400 mL) and distilled water (400 mL). The organic layer was collected, dried over $Na_2SO_4$, filtered and concentrated on rotary evaporator. The resulting solid was used for subsequent steps without further purification.

Synthesis of N-arylated intermediate (4)

A mixture of 5-nitroindole (2, 12.82 g, 79.06 mmol), compound 3 (17 g, 79.06 mmol), KOH (8.87 g, 158.12 mmol), KI (1.31 g, 7.906 mmol) and DMSO (170 mL) were charged in a round bottom flask under $N_{2\,(g)}$, stirred at 110° C. for 8 hours. Once completion of reaction was confirmed, the mixture was left to cool to room temperature, crushed with ice-water (1 L), acidified using 6N HCl to pH 4-5, and stirred at room temperature for 30 minutes. The product was filtered and washed with water, dried on rotary evaporator. The resulting crude would further be purified with column chromatography and used for subsequent steps.

$^1$H NMR (DMSO-$d_6$, 500 MHz) δ 8.94 (d, 1H, J=4.8 Hz), 8.83 (d, 1H, J=5.6 Hz), 8.71 (d, 1H, J=2.0 Hz), 8.23 (d, 1H, J=2.4 Hz), 8.18-8.15 (m, 2H), 7.98-7.92 (m, 2H), 7.11 (s, 1H), 2.87 (d, 3H, J=4.8 Hz); LC-MS: 297.16 (M$^+$+1).

Reduction of 5-Nitroindole Derivative (Synthesis of the Amino Intermediate 5)

To a solution of compound 4 (593 mg, 2 mmol) in anhydrous DMF (5 mL), 5% Pd/C (60 mg) was added. It was then stirred and bubbled with $H_{2\,(g)}$ at room temperature for 2-3 hours. Once the reaction finished, the mixture was filtered through celite. The filtrate was crushed with ice-water, filtered, and the resulting solid was dried and used for the next steps without further purification.

$^1$H NMR (DMSO-$d_6$, 500 MHz) δ 8.86 (q, 1H, J=4.5 Hz), 8.67-8.66 (m, 1H), 8.17 (d, 1H, J=2.5 Hz), 7.81 (dd, 1H, J=2.0, 5.5 Hz), 7.75 (d, 1H, J=3.0 Hz), 7.54 (d, 1H, J=8.5 Hz), 6.80 (d, 1H, J=2.0 Hz), 6.67 (dd, 1H, J=2.0, 8.5 Hz), 6.57 (dd, 1H, J=0.5, 3.5 Hz), 4.86 (s, 2H), 2.86 (d, 3H, J=5.0 Hz); $^{13}$C NMR (DMSO-$d_6$, 125 MHz) δ 164.0, 151.9, 150.1, 147.3, 143.7, 131.6, 127.4, 127.0, 117.6, 113.0, 112.8, 111.4, 105.7, 104.3.

Synthesis of Urea and Thiourea Derivatives Via Reaction of Amine Intermediate (5) with Isocyanate or Isothiocyanate Reagents A solution of compound 5 (100 mg, 0.38 mmol) was dissolved in anhydrous THF (2 mL) and charged with isocyanate or isothiocyanate derivative (0.57 mmol). This mixture was stirred overnight under $N_{2\ (g)}$ at room temperature. The reaction was monitored by TLC and LC-MS. Upon completion, the mixture was then dried by the rotary evaporator and purified by column chromatography (silica gel, hexane/ethyl acetate).

Synthesis of Urea Derivatives 1g and 1h Via Carbamate Intermediate

Compound 5 (300 mg, 1.13 mmol) was dissolved in anhydrous THF (3 mL), cooled to 0° C., and stirred under $N_{2\ (g)}$. TEA (392 μL, 2.82 mmol) was then added to the mixture and stirred for 15 minutes. Next, phenyl chloroformate (220 μL, 1.7 mmol) dissolved in anhydrous THF (1 mL) was added in a dropwise manner to the mixture at 0° C. The mixture was then stirred at room temperature and was monitored by TLC and mass spectrometry. Once the amine starting material was completely consumed, the mixture was dried by the rotary evaporator and purified by column chromatography (silica gel, hexane/ethyl acetate).

The resulting carbamate would be used for subsequent urea formation. The relevant amine reagent possessing morpholine or N-methylpiperazine (0.89 mmol) was dissolved in anhydrous DMF (2 mL), charged with Hunig's base (214 μL, 1.23 mmol), and stirred under $N_{2\ (g)}$ at room temperature. Later, a solution of carbamate 6 (193 mg, 0.50 mmol) in anhydrous DMF (2 mL) was added to the mixture. The mixture was heated and stirred at 80° C. under $N_{2\ (g)}$ and monitored every 10 minutes via TLC. Upon reaction completion, the product was cooled to room temperature, crushed with ice, and extracted with ethyl acetate (25 mL) and saline (25 mL). The organic layer was dried over anhydrous $Na_2SO_4$, concentrated using the rotary evaporator, and purified using column chromatography (silica gel, hexane/ethyl acetate).

Amidation of Compound (5) with Carboxylic Acid

A solution of compound 5 (100 mg, 0.38 mmol) in anhydrous THF (2 mL) was cooled to 0° C. and stirred under $N_{2\ (g)}$. TEA (33 μL, 0.95 mmol) was then added to the mixture and stirred for 15 minutes. Next, HOBt, (77 mg, 0.57 mmol) and EDCI.HCl (88 mg, 0.57 mmol) were added to the mixture and stirred for another 15 minutes at room temperature. This was followed by the dropwise addition of the appropriate carboxylic acid derivative (0.57 mmol) dissolved in anhydrous THF (1 mL), and the reaction mixture was kept under stirring at room temperature overnight. Upon reaction completion, the mixture was dried by the rotary evaporator, extracted with ethyl acetate (25 mL) and water (25 mL), and purified by column chromatography (silica gel, hexane/ethyl acetate).

Amidation of Compound 5 with Acyl Chloride

A solution of compound 5 (100 mg, 0.38 mmol) in anhydrous THF (2 mL) was cooled to 0° C. and stirred under $N_{2\ (g)}$. TEA (0.95 mmol, 33 μL) was then added to the mixture and stirred for 15 minutes. This was followed by the addition of the acyl chloride (0.57 mmol) dissolved in anhydrous THF (1 mL) in a dropwise manner at 0° C. The reaction was monitored by TLC and mass spectrometry. Upon reaction completion, the mixture was dried by rotary evaporator and purified by column chromatography (silica gel, hexane/ethyl acetate).

Synthesis of the Target Sulfonamide Derivatives 1p-t

A solution of compound 5 (100 mg, 0.38 mmol) in anhydrous THF (2 mL) was cooled to 0° C. and stirred under $N_{2\ (g)}$. TEA (0.95 mmol, 33 μL) was added thereto, and the reaction mixture was left under stirring at room temperature for 15 minutes. A sulfonyl chloride derivative (0.76 mmol) dissolved in THF (1 mL) was added dropwise to the mixture at 0° C. The reaction was stirred at room temperature for 4-12 hours. Upon reaction completion, the mixture was dried by rotary evaporator. The crude compound was then extracted by ethyl acetate (25 mL) and distilled water (25 mL). The organic layer was collected, dried over $Na_2SO_4$, and filtered. The filtrate was dried over rotary evaporator. The compound was further purified using column chromatography (silica gel, hexane/ethyl acetate).

Spectral Data of the Target Compounds 1a-y

Compound 1a: Yield: 81%; mp: 211-214° C.; $^1$H NMR (DMSO-$d_6$, 500 MHz) δ 8.87 (d, 1H, J=5.0 Hz), 8.72-8.69 (m, 3H), 8.21 (d, 1H, j=2.0 Hz), 7.90-7.87 (m, 3H), 7.73 (d, 1H, j=9.0 Hz), 7.48 (d, 2H, j=8.0 Hz), 7.29-7.26 (m, 3H), 6.96 (t, 1H, j=7.5 Hz), 6.78 (d, 1H, j=3.0 Hz), 2.87 (d, 3H, J=4.5 Hz); $^{13}$C NMR (DMSO-$d_6$, 125 MHz) δ 163.9, 152.9, 152.1, 150.3, 147.1, 139.9, 134.1, 130.7, 130.2, 128.8, 128.0, 121.6, 118.3, 118.1, 115.9, 113.7, 111.2, 110.5, 106.3, 26.1; LC/MS m/z: 386.07 (M$^+$+1).

Compound 1b: Yield: 40%; mp: 202-204° C.; $^1$H NMR (DMSO-$d_6$, 500 MHz) δ 9.53 (brs, 1H), 9.33 (brs, 1H), 8.88 (q, 1H, j=4.5 Hz), 8.73 (d, 1H, j=5.5 Hz), 8.22 (d, 1H, j=2.0 Hz), 7.94 (d, 1H, j=2.5 Hz), 7.91-7.88 (m, 3H), 7.74 (d, 1H, j=8.5 Hz), 7.51 (d, 1H, j=9.0 Hz), 7.38 (dd, 1H, j=3.0, 8.5 Hz), 7.34 (dd, 1H, j=2.0, 9.0 Hz), 6.79 (d, 1H, j=3.0 Hz), 2.87 (d, 3H, j=5.0 Hz); $^{13}$C NMR (DMSO-$d_6$, 125 MHz) δ 163.9, 152.8, 152.1, 150.3, 147.1, 140.5, 133.9, 130.9, 130.6, 130.5, 130.3, 128.0, 122.6, 119.1, 118.3, 118.2, 116.1, 113.7, 111.1, 110.8, 106.3, 26.1; LC/MS m/z: 454.12 (M$^+$+1).

Compound 1c: Yield: 24%; mp: 212-215° C.; $^1$H NMR (DMSO-$d_6$, 500 MHz) δ 9.02 (brs, 1H), 8.87 (q, 1H, j=4.5 Hz), 8.80 (s, 1H), 8.72 (d, 1H, j=5.5 Hz), 8.22 (d, 1H, j=2.5 Hz), 8.06 (s, 1H), 7.92-7.90 (m, 2H), 7.88 (dd, 1H, 7=2, 5.5 Hz), 7.75 (d, 1H, J=9.0 Hz), 7.59-7.58 (m, 1H), 7.51 (t, 1H, J=3.0 Hz), 7.32-7.29 (m, 2H), 6.79 (d, 1H, J=3.5 Hz), 2.87 (d, 3H, J=5.0 Hz); $^{13}$C NMR (DMSO-$d_6$, 125 MHz) δ 163.9, 153.4, 152.1, 150.3, 150.1, 147.1, 140.8, 133.6, 130.6, 130.4, 129.9, 129.5 (d, J=31.2 Hz), 128.1, 124.2 (d, J=271.2 Hz), 121.7, 118.3, 117.8, 116.1, 114.0 (d, J=3.7 Hz), 113.7, 111.2, 110.9, 106.3, 26.1; LC/MS m/z: 454.12 (M$^+$+1).

Compound 1d: Yield: 42%; mp: 235-238° C.; $^1$H NMR (DMSO-$d_6$, 500 MHz) δ 9.12 (brs, 1H), 8.87 (q, 1H, 7=4.5 Hz), 8.83 (s, 1H), 8.72 (d, 1H, 7=5.5 Hz), 8.21 (d, 1H, 7=2.0 Hz), 8.15 (d, 1H, 7=2.5 Hz), 7.91-7.90 (m, 2H), 7.88 (dd, 1H, 7=2.5, 5.5 Hz), 7.74 (d, 1H, 7=9.0 Hz), 7.64-7.60 (m, 2H), 7.30 (dd, 1H, 7=2.0, 9.0 Hz), 6.80-6.79 (m, 1H), 2.87 (d, 3H, 7=5.0 Hz); $^{13}$C NMR (DMSO-$d_6$, 125 MHz) δ 163.9, 152.7, 152.1, 150.3, 147.1, 139.6, 133.4, 132.0, 130.6, 130.5, 128.1, 126.9 (d, 7=30.0 Hz), 122.9, 122.8 (d, 7=272.5 Hz), 122.0 (d, 7=1.25 Hz), 118.4, 116.7 (d, 7=6.2 Hz), 116.2, 113.8, 111.2, 111.1, 106.3, 26.1; LC/MS w/z: 488.08 (M$^+$+1).

Compound 1e: Yield: 45%; mp: 208-211° C.; $^1$H NMR (DMSO-$d_6$, 500 MHz) δ 9.55 (brs, 1H), 9.24 (brs, 1H), 8.88-8.87 (m, 1H), 8.72 (d, 1H, 7=5.5 Hz), 8.21 (d, 1H, 7=2.0 Hz), 8.07-8.06 (m, 1H), 7.91-7.87 (m, 3H), 7.73 (d, 1H, 7=9.0 Hz), 7.68-7.66 (m, 1H), 7.44-7.40 (m, 1H), 7.34-7.32 (m, 1H), 6.78 (d, 1H, 7=3.5 Hz), 2.87 (d, 3H, 7=5.0 Hz); $^{13}$C NMR (DMSO-$d_6$, 125 MHz) δ 163.9, 153.3 (d, 7=248.7 Hz), 153.0, 152.1, 150.3, 147.1, 137.1 (d, 7=2.5

Hz), 133.9, 130.5 (d, J=32.5 Hz), 128.0, 124.0 (d, J=7.5 Hz), 122.7 (d, J=270 Hz), 118.3, 117.5 (d, J=21.2 Hz), 116.2, 116.1, 115.7, 115.7, 113.7, 111.1, 110.9, 106.3, 26.1; LC/MS m/z: 471.76 (M$^+$+1).

Compound 1f: Yield: 44%; mp: 218-221° C.; $^1$H NMR (DMSO-d$_6$, 500 MHz) δ 10.80 (brs, 2H), 8.88 (s, 1H), 8.72 (d, 1H, J=5.5 Hz), 8.25 (s, 2H), 8.20 (d, 1H, J=2.0 Hz), 7.98 (s, 1H), 7.89-7.86 (m, 2H), 7.70-7.68 (m, 1H), 7.53 (s, 1H), 7.42 (d, 1H, J=9.0 Hz), 6.76-7.65 (m, 1H), 2.87 (s, 3H); $^{13}$C NMR (DMSO-d$_6$, 125 MHz) δ 163.9, 153.4, 152.1, 150.3, 150.1, 147.1, 143.2, 134.4, 130.9, 130.5 (d, J=31.2 Hz), 130.5, 130.2, 127.9, 127.8, 123.4 (q, J=271.2 Hz), 118.3, 118.1, 117.5, 116.1, 113.7, 113.7, 113.2, 110.9, 110.8, 106.3, 26.1; LC/MS m/z: 522.04 (M$^+$+1).

Compound 1g: Yield: 35%; mp: 247-250° C.; $^1$H NMR (DMSO-d$_6$, 500 MHz) δ 9.01 (brs, 1H), 8.88 (q, 1H, J=4.5 Hz), 8.82 (s, 1H), 8.72 (d, 1H, J=5.5 Hz), 8.21 (d, 1H, J=2.0 Hz), 7.95 (d, 1H, J=2.5 Hz), 7.91-7.87 (m, 3H), 7.74 (d, 1H, J=9.0 Hz), 7.63-7.60 (m, 1H), 7.53-7.52 (m, 1H), 7.30 (dd, 1H, J=2.0, 8.5 Hz), 6.79 (d, 1H, J=3.5 Hz), 3.69 (t, 4H, J=5.0 Hz), 2.87 (d, 3H, J=5.0 Hz), 2.81-2.81 (t, 4H, J=4.5 Hz); $^{13}$C NMR (DMSO-d$_6$, 125 MHz) δ 164.0, 152.9, 152.1, 150.4, 147.2, 145.6, 137.5, 133.8, 130.7, 130.7, 128.1, 126.4 (d, J=27.5 Hz), 125.5, 124.0 (d, J=271.2 Hz), 122.8, 118.4, 116.1, 116.0, 113.8, 111.3, 110.9, 106.4, 66.8, 53.6, 26.2; LC/MS m/z: 539.11 (M$^+$+1).

Compound 1h: Yield: 43%; $^1$H NMR (DMSO-d$_6$, 500 MHz) δ 9.02 (brs, 1H), 8.88 (d, 1H, J=5.0 Hz), 8.87 (brs, 1H), 8.71 (d, 1H, J=5.5 Hz), 8.21 (d, 1H, J=2.0 Hz), 7.94-7.87 (m, 4H), 7.73 (d, 1H, J=9.0 Hz), 7.59 (dd, 1H, J=2.0, 9.0 Hz), 7.49 (d, 1H, J=8.5 Hz), 7.29 (dd, 1H, J=2.0, 9.0 Hz), 6.78 (d, 1H, J=3.5 Hz), 2.86 (d, 3H, J=4.5 Hz), 2.80 (brs, 4H), 2.43 (brs, 4H), 2.21 (s, 3H); $^{13}$C NMR (DMSO-d$_6$, 125 MHz) δ 163.9, 152.9, 152.1, 150.3, 147.1, 145.9, 137.3, 133.8, 130.7, 130.3, 128.1, 126.3, 125.3, 125.1, 124.1, 122.7, 118.3, 116.0, 113.8, 111.2, 110.8, 106.3, 55.2, 53.2, 45.9, 26.1; LC/MS m/z: 552.47 (M$^+$+1).

Compound 1i: Yield: 98%; mp: 248-251° C.; $^1$H NMR (CDCl$_3$, 500 MHz) δ 8.34 (d, 1H, J=5.5 Hz), 8.11 (d, 3H, J=11.0 Hz), 7.92 (d, 2H, J=7.0 Hz), 7.70 (d, 1H, J=9.0 Hz), 7.57 (dd, 2H, J=2.5, 5.5 Hz), 7.56-7.44 (m, 3H), 7.40 (dd, 2H, J=1.5, 9.0 Hz), 6.72 (d, 1H, J=3.5 Hz), 3.07 (d, 3H, J=5.0 Hz); $^{13}$C NMR (CDCl$_3$, 125 MHz) δ 166.0, 164.6, 152.2, 149.8, 148.1, 135.3, 132.5, 132.3, 131.8, 131.0, 130.2, 128.9, 128.5, 127.4, 127.2, 118.5, 117.6, 115.1, 113.7, 111.4, 107.0; LC/MS m/z: 371.08 (M$^+$+1).

Compound 1j: Yield: 76%; mp: 211-213° C.; $^1$H NMR (DMSO-d$_6$, 500 MHz) δ 10.44 (brs, 1H), 8.89 (d, 1H, J=5.0 Hz), 8.74 (d, 1H, J=5.5 Hz), 8.26-8.21 (m, 3H), 7.99-7.90 (m, 3H), 7.84-7.80 (m, 2H), 7.62-7.60 (m, 1H), 6.86 (d, 1H, J=3.0 Hz), 2.88 (d, 3H, J=5.0 Hz); $^{13}$C NMR (DMSO-d$_6$, 125 MHz) δ 163.9, 163.0, 152.1, 150.3, 147.1, 135.4, 134.2, 133.0, 131.3, 130.7, 130.3, 129.6, 128.3, 128.0, 118.6, 117.5, 114.0, 113.1, 111.0, 106.5; LC/MS m/z: 439.00 (M$^+$+1).

Compound 1k: Yield: 64%; mp: 220-221° C.; $^1$H NMR (DMSO-d$_6$, 500 MHz) δ 10.53 (brs, 1H), 8.89 (d, 1H, J=5.0 Hz), 8.75 (d, 1H, J=5.5 Hz), 8.34-8.31 (m, 2H), 8.24-8.22 (m, 2H), 7.98-7.95 (m, 3H), 7.93-7.91 (m, 2H), 7.63 (dd, 1H, J=1.5, 8.5 Hz), 6.87 (d, 1H, J=3.5 Hz), 2.88 (d, 3H, J=5.0 Hz); $^{13}$C NMR (DMSO-d$_6$, 125 MHz) δ 163.9, 163.8, 152.1, 150.3, 147.1, 136.0, 133.0, 131.8, 131.3, 130.3, 129.7, 129.3, 129.1, 128.3, 128.0, 125.1, 124.2, 123.0, 118.6, 117.6, 114.0, 113.2, 111.0, 106.4; LC/MS m/z: 439.12 (M$^+$+1).

Compound 1l: Yield: 69%; mp: 255-258° C.; $^1$H NMR (DMSO-d$_6$, 500 MHz) δ 10.56 (brs, 1H), 8.88 (dd, 1H, J=4.5, 9.5 Hz), 8.74 (d, 1H, J=5.5 Hz), 8.43 (d, 1H, J=1.5 Hz), 8.30 (dd, 1H, J=2.0, 8.5 Hz), 8.23-8.20 (m, 2H), 7.95-7.90 (m, 3H), 7.82 (d, 1H, J=8.5 Hz), 7.60 (dd, 1H, J=2.0, 9.0 Hz), 6.86 (d, 1H, J=3.0 Hz), 2.87 (d, 3H, J=5.0 Hz); $^{13}$C NMR (DMSO-d$_6$, 125 MHz) δ 163.9, 162.9, 152.1, 150.3, 147.0, 134.3, 133.7, 133.3, 132.9, 131.9, 131.3, 130.2, 128.3, 127.0 (d, J=5.0 Hz), 126.8, 126.5, 121.6, 118.6, 117.5, 114.0, 113.2, 111.0, 106.4; LC/MS m/z: 473.21 (M$^+$+1).

Compound 1m: Yield: 64%; mp: 260-263° C.; $^1$H NMR (DMSO-d$_6$, 500 MHz) δ 10.50 (brs, 1H), 8.89 (d, 1H, J=5.0 Hz), 8.75 (d, 1H, J=5.5 Hz), 8.41-8.39 (m, 2H), 8.22 (dd, 2H, J=2.0, 20.0 Hz), 7.96-7.91 (m, 2H), 7.82 (d, 1H, J=9.0 Hz), 7.74-7.70 (m, 1H), 7.60 (dd, 1H, J=2.0, 9.0 Hz), 6.87 (d, 1H, J=3.0 Hz), 2.88 (d, 3H, J=5.0 Hz); $^{13}$C NMR (DMSO-d$_6$, 125 MHz) δ 163.9, 162.9, 159.5, 152.1, 150.3, 147.0, 135.0 (J=9.6 Hz), 132.9, 131.9, 131.9, 131.3, 130.3, 128.3, 126.9 (d, J=3.0 Hz), 123.5, 121.3, 118.6, 117.6 (d, J=4.1 Hz), 117.4, 116.4 (d, J=13.8 Hz), 114.0, 113.2, 111.0, 106.4; LC/MS m/z: 457.14 (M$^+$+1).

Compound 1n: Yield: 54%; mp: 258-261° C.; $^1$H NMR (DMSO-d$_6$, 500 MHz) δ 10.71 (brs, 1H), 8.89 (d, 1H, J=5.0 Hz), 8.74 (d, 1H, J=5.5 Hz), 8.65 (s, 2H), 8.36 (s, 1H), 8.22 (dd, 2H, J=2.0, 12.0 Hz), 7.96-7.91 (m, 2H), 7.84 (d, 1H, J=8.5 Hz), 7.61 (dd, 1H, J=1.5, 8.5 Hz), 6.87 (d, 1H, J=3.5 Hz), 2.87 (d, 3H, J=4.5 Hz); $^{13}$C NMR (DMSO-d$_6$, 125 MHz) δ 163.9, 162.3, 152.1, 150.3, 147.0, 137.3, 132.7, 131.4, 130.9, 130.6, 130.3 (d, J=10.6 Hz), 130.1, 128.5 (d, J=10.9 Hz), 126.4, 125.0, 124.2, 122.1, 118.6, 117.6, 114.0, 113.4, 111.1, 106.4; LC/MS m/z: 507.10 (M$^+$+1).

Compound 1o: Yield: 58%; mp: 237-240° C.; $^1$H NMR (DMSO-d$_6$, 500 MHz) δ 10.42 (brs, 1H), 8.88 (d, 1H, J=5.0 Hz), 8.74 (d, 1H, J=5.5 Hz), 8.29-8.19 (m, 4H), 7.94-7.90 (m, 2H), 7.81 (d, 1H, J=9.0 Hz), 7.66-7.59 (m, 2H), 6.85 (d, 1H, J=3.0 Hz), 3.74 (t, 4H, J=5.0 Hz), 2.96 (t, 4H, J=4.5 Hz), 2.87 (d, 3H, J=4.5 Hz); $^{13}$C NMR (DMSO-d$_6$, 125 MHz) δ 163.9, 163.6, 154.3, 152.1, 150.3, 147.1, 133.2, 132.9, 131.2, 130.9, 130.3, 128.3, 126.9 (d, J=5.3 Hz), 125.0, 124.5, 124.3, 123.8, 122.9, 118.5, 117.6, 113.9, 113.1, 111.0, 106.4; LC/MS m/z: 524.18 (M$^+$+1).

Compound 1p: Yield: 51%; mp: 198-200° C.; $^1$H NMR (CDCl$_3$, 500 MHz) δ 8.61 (d, 1H, J=5.5 Hz), 8.31 (d, 1H, J=2.0 Hz), 8.10 (d, 1H, J=4.5 Hz), 7.73 (dd, 2H, J=1.0, 8.5 Hz), 7.57 (d, 1H, J=9.0 Hz), 7.53-7.47 (m, 2H), 7.45-7.42 (m, 2H), 7.40-7.37 (m, 2H), 6.95-6.92 (m, 2H), 6.67-6.66 (m, 1H), 3.07 (d, 3H, J=5.0 Hz); $^{13}$C NMR (CDCl$_3$, 125 MHz) δ 164.3, 152.0, 149.7, 148.1, 139.3, 133.3, 133.0, 131.1, 130.5, 129.1, 127.7, 127.4, 120.1, 118.7, 117.0, 115.4, 111.6, 106.9; LC/MS m/z: 407.05 (M$^+$+1).

Compound 1q: Yield: 60%; mp: 93-95° C.; $^1$H NMR (CDCl$_3$, 500 MHz) δ 8.62 (d, 1H, J=5.5 Hz), 8.32 (d, 1H, J=2.0 Hz), 8.14 (d, 1H, J=4.5 Hz), 7.88 (d, 1H, J=2.0 Hz), 7.60-7.43 (m, 6H), 7.35 (s, 1H), 6.97 (d, 1H, J=8.0 Hz), 6.68 (d, 1H, J=3.5 Hz), 3.09 (d, 3H, J=5.0 Hz); $^{13}$C NMR (CDCl$_3$, 125 MHz) δ 164.5, 152.1, 149.9, 147.9, 139.2, 137.7, 133.7, 133.4, 131.1, 129.8, 129.3, 128.0, 126.6, 120.1, 118.8, 117.2, 115.4, 111.7, 106.8; LC/MS m/z: 475.04 (M$^+$+1).

Compound 1r: Yield: 78%; mp: 79-81° C.; $^1$H NMR (CDCl$_3$, 500 MHz) δ 8.61 (d, 1H, J=5.5 Hz), 8.30 (d, 1H, J=1.5 Hz), 8.14 (d, 1H, J=4.5 Hz), 8.04 (s, 1H), 7.86 (d, 1H, J=7.5 Hz), 7.74 (d, 1H, J=8.0 Hz), 7.57 (d, 1H, J=8.5 Hz), 7.53-7.49 (m, 2H), 7.46-7.43 (m, 2H), 7.35 (s, 1H), 6.95 (d, 1H, J=8.5 Hz), 6.66 (d, 1H, J=3.0 Hz), 3.09 (d, 3H, J=5.0 Hz); $^{13}$C NMR (CDCl$_3$, 125 MHz) δ 164.5, 152.1, 149.9, 147.9, 140.6, 133.4, 131.8, 131.6, 131.3, 131.1, 130.7, 129.9, 129.8, 129.5 (d, J=3.4 Hz), 128.0, 124.6, 124.5 (d, J=3.8 Hz), 124.3, 122.2, 120.2, 118.8, 117.4, 115.4, 111.7, 106.8; LC/MS m/z: 475.04 (M$^+$+1).

Compound 1s: Yield: 99%; mp: 99-102° C.; $^1$H NMR (CDCl$_3$, 500 MHz) δ 8.62 (d, 1H, J=5.5 Hz), 8.31 (d, 1H, j=2.0 Hz), 8.15-8.10 (m, 2H), 7.76 (dd, 1H, j=1.5, 8.5 Hz), 7.58 (d, 1H, j=8.5 Hz), 7.54-7.44 (m, 5H), 6.96 (d, 1H, j=8.5 Hz), 6.67 (d, 1H, j=3.0 Hz), 3.09 (d, 3H, J=5.0 Hz); $^{13}$C NMR (CDCl$_3$, 125 MHz) δ 164.6, 152.1, 150.0, 147.9, 138.6, 137.4, 133.5, 132.3, 131.7, 131.1, 129.6, 129.6, 129.3, 128.1, 126.9, 126.8, 126.8, 126.8, 123.2, 121.0, 120.2, 118.9, 117.3, 115.4, 111.8, 106.7; LC/MS m/z: 509.06 (M$^+$+1).

Compound 1t: Yield: 39%; mp: 210-213° C.; $^1$H NMR (DMSO-d$_6$, 500 MHz) δ 10.42 (brs, 1H), 8.86 (d, 1H, j=5.0 Hz), 8.71 (d, 1H, j=5.5 Hz), 8.45 (s, 1H), 8.22 (s, 2H), 8.14 (d, 1H, j=2.0 Hz), 7.92 (d, 1H, j=3.5 Hz), 7.82 (dd, 1H, j=2.5, 5.5 Hz), 7.70 (d, 1H, j=8.5 Hz), 7.41 (d, 1H, j=2.0 Hz), 6.99 (dd, 1H, j=1.5, 8.5 Hz), 6.79 (d, 1H, j=3.5 Hz), 2.85 (d, 3H, J=5.0 Hz); $^{13}$C NMR (CDCl$_3$, 125 MHz) δ 163.8, 152.1, 150.3, 146.8, 141.9, 132.3, 131.7, 131.4, 131.1, 130.9, 130.6, 130.2, 129.0, 127.3, 126.9, 125.7, 123.5, 121.4, 119.2, 118.9, 118.8, 115.4, 114.3, 111.7, 106.1; LC/MS m/z: 543.08 (M$^+$+1).

Compound 1u: Yield: 32%; mp: 111-114° C.; $^1$H NMR (DMSO-d$_6$, 500 MHz) δ 9.90 (brs, 1H), 9.76 (brs, 1H), 8.88 (d, 1H, j=4.5 Hz), 8.74 (d, 1H, j=5.0 Hz), 8.22 (d, 1H, j=2.0 Hz), 7.94-7.89 (m, 2H), 7.79-7.76 (m, 2H), 7.52 (d, 2H, j=7.5 Hz), 7.34-7.31 (m, 3H), 7.13-7.12 (m, 1H), 6.84 (d, 1H, j=3.5 Hz), 2.87 (d, 3H, j=4.5 Hz); $^{13}$C NMR (DMSO-d$_6$, 125 MHz) δ 163.8, 152.1, 150.3, 147.0, 139.7, 133.4, 131.9, 130.2, 128.3, 128.3, 124.3, 123.7, 121.2, 118.6, 117.2, 114.1, 110.9, 106.4; LC/MS m/z: 402.01 (M$^+$+1).

Compound 1v: Yield: 46%; mp: 117-120° C.; $^1$H NMR (DMSO-d$_6$, 500 MHz) δ 10.10 (brs, 1H), 9.83 (brs, 1H), 8.88 (d, 1H, J=5.0 Hz), 8.75 (d, 1H, J=5.5 Hz), 8.22 (d, 1H, J=2.0 Hz), 7.95-7.89 (m, 3H), 7.79-7.75 (m, 2H), 7.56 (d, 1H, J=8.5 Hz), 7.48 (dd, 1H, J=2.5, 9.0 Hz), 7.30 (dd, 1H, 7=1.5, 8.5 Hz), 6.85 (d, 1H, J=3.5 Hz), 2.87 (d, 3H, J=5.0 Hz); $^{13}$C NMR (DMSO-d$_6$, 125 MHz) δ 163.7, 152.1, 150.2, 147.0, 139.6, 133.4, 131.8, 130.1, 128.3, 128.2, 124.3, 123.6, 121.2, 118.5, 117.2, 114.0, 110.8, 106.3; LC/MS m/z: 469.99 (M$^+$+1).

Compound 1w: Yield: 37%; mp: 165-168° C.; $^1$H NMR (DMSO-d$_6$, 500 MHz) δ 10.10 (brs, 1H), 9.87 (brs, 1H), 8.89 (d, 1H, J=5.0 Hz), 8.75 (d, 1H, J=5.5 Hz), 8.22 (d, 1H, 7=2.0 Hz), 7.98-7.95 (m, 2H), 7.90 (dd, 1H, J=2.5, 5.5 Hz), 7.80-7.76 (m, 3H), 7.56-7.53 (m, 1H), 7.44 (d, 1H, J=8.0 Hz), 7.32 (dd, 1H, J=2.0, 9.0 Hz), 6.85 (d, 1H, 7=3.0 Hz), 2.87 (d, 3H, J=5.0 Hz); $^{13}$C NMR (DMSO-d$_6$, 125 MHz) δ 180.1, 163.8, 152.1, 150.3, 147.0, 140.7, 132.8, 132.2, 130.3, 129.3, 129.2, 129.0, 128.7, 128.4, 127.4, 125.2, 123.0, 121.2, 120.4, 119.9, 118.7, 117.4, 114.1, 111.1, 106.4; LC/MS m/z: 470.12 (M$^+$+1).

Compound 1x: Yield: 41%; mp: 171-174° C.; $^1$H NMR (DMSO-d$_6$, 500 MHz) δ 11.02 (brs, 2H), 8.88 (d, 1H, J=4.5 Hz), 8.74 (d, 1H, J=5.0 Hz), 8.22 (d, 2H, J=2.0 Hz), 7.94-7.89 (m, 3H), 7.81-7.75 (m, 2H), 7.62 (d, 1H, J=9.0 Hz), 7.36 (dd, 1H, J=1.5, 9.0 Hz), 6.83 (d, 1H, 7=3.5 Hz), 2.87 (d, 3H, 7=5.0 Hz); $^{13}$C NMR (DMSO-d$_6$, 125 MHz) δ 179.5, 175.4, 163.9, 152.1, 150.3, 147.1, 140.5, 133.6, 131.8, 131.2, 130.2, 128.2, 128.1, 126.3, 126.1, 125.8, 125.5, 124.0, 123.9, 122.0, 121.8, 121.0, 118.6, 116.9, 114.0, 110.8, 106.4; LC/MS m/r 504.02 (M$^+$+1).

Compound 1y: Yield: 26%; mp: 210-213° C.; $^1$H NMR (DMSO-d$_6$, 500 MHz) δ 10.35 (brs, 1H), 10.06 (brs, 1H), 8.89 (d, 1H, J=4.5 Hz), 8.75 (d, 1H, J=5.5 Hz), 8.28 (s, 2H), 8.23 (s, 1H), 7.97 (d, 1H, J=3.0 Hz), 7.90 (d, 1H, J=3.5 Hz), 7.82-7.75 (m, 3H), 7.31 (d, 1H, J=8.5 Hz), 6.86 (d, 1H, j=3.0 Hz), 2.87 (d, 3H, j=4.5 Hz); $^{13}$C NMR (DMSO-d$_6$, 125 MHz) δ 180.1, 163.8, 152.2, 150.4, 147.0, 142.1, 132.4, 132.4, 130.4, 130.3, 130.0, 129.7, 129.5, 128.6, 126.5, 124.4, 123.7, 122.2, 121.3, 120.0, 118.8, 177.7, 116.7, 114.2, 111.3, 106.4; LC/MS m/z: 538.04 (M$^+$+1).

Experimental Examples

Antiproliferative Activity
Cell Culture

In this study, two hepatocellular carcinoma cell lines (Hep3B & Huh7) were used for screening the antiproliferative activity of the target molecules. Both cell lines were obtained from the European Collection of Cell Cultures (ECACC, UK) and maintained in Roswell Park Memorial Institute medium (RPMI, Sigma-Aldrich, St. Louis, Mo., USA). All media were supplemented with 10% fetal bovine serum (FBS, Sigma-Aldrich) and 1% penicillin/streptomycin (Sigma-Aldrich). All incubations were done at 37° C. in a humidified atmosphere of 5% CO$_2$.

Cell Viability Assay

MTT assay was performed to assess the effect of the synthesized compounds on cell viability and to determine the half-maximal inhibitory concentration (IC$_{50}$) of the most active compounds as mentioned before with some minor modifications. The cells were seeded in 96-well tissue culture plates with a density of 4×10$^4$/well and incubated overnight. After that, cells were treated with the newly synthesized compounds or Sorafenib as a positive control for 48 h. DMSO (vehicle) was used as a negative control. After treatment, the media was removed, and cells were incubated for 2 h at 37° C. with 200 μL media containing 0.5 mg/mL of MTT tetrazolium dye (Sigma-Aldrich). Finally, the media were removed and 200 μL of DMSO was added to solubilize the formed violet crystals. Absorbance was measured at 570 nm using a microplate reader (Thermo Scientific, Massachusetts, USA).

Kinase Profiling

In a final reaction volume of 25 μL, kinase (5-10 mU) is incubated with 25 mM Tris pH 7.5, 0.02 mM EGTA, 0.66 mg/mL myelin basic protein, 10 mM magnesium acetate and [γ$^{33}$P-ATP] (specific activity approx. 500 cpm/pmol, concentration as required). The reaction is initiated by the addition of the Mg-ATP mix. After incubation for 40 min at room temperature, the reaction is stopped by the addition of 5 μL of a 3% phosphoric acid solution. 10 μL of the reaction is then spotted onto a P30 filtermat and washed three times for 5 min in 75 mM phosphoric acid and once in methanol prior to drying and scintillation counting.

What is claimed is:
1. A compound according to formula I, or a pharmaceutically acceptable salt thereof:

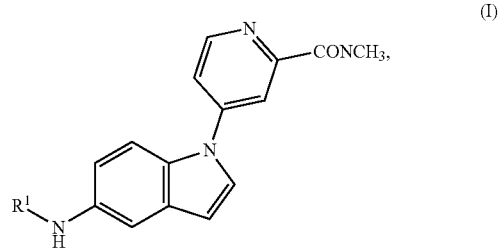

wherein R¹ is -(L)-R², wherein L is selected from a group consisting of: a covalent bond, —C(O), —C(O)—NH—, —C(S)—NH—, and —S(O₂)—, wherein R² is an alkyl, cycloalkyl, adamantyl, or (substituted) aryl group of formula II:

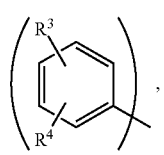

(II)

and wherein R³ and R⁴ are independently selected from a group consisting of: halogen, C1-C5 alkyl, C1-C5 alkyl substituted with 1, 2, or 3 halogen atoms, C3-C10 cycloalkyl, morpholino optionally substituted with C1-C5 alkyl, and piperazine optionally substituted with C1-C5 alkyl.

2. The compound of claim 1, or a pharmaceutically acceptable salt thereof, wherein the compound is of formula I.A:

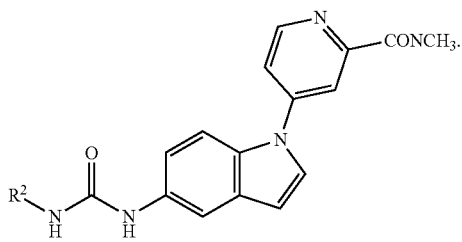

(I.A)

3. The compound of claim 1, or a pharmaceutically acceptable salt thereof, wherein the compound is of formula I.B:

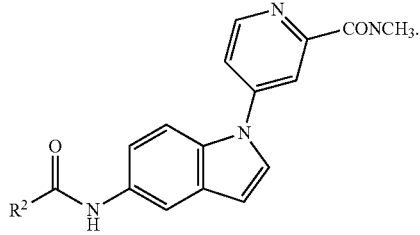

(I.B)

4. The compound of claim 1, or a pharmaceutically acceptable salt thereof, wherein the compound is of formula I.C:

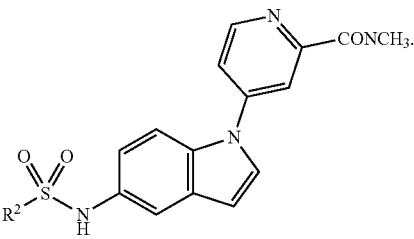

(I.C)

5. The compound of claim 1, or a pharmaceutically acceptable salt thereof, wherein the compound is of Formula I.D:

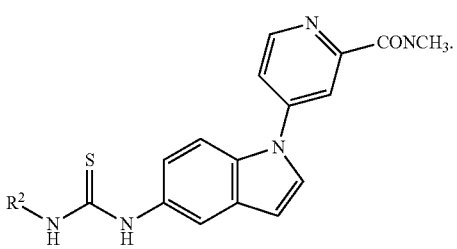

(I.D)

6. A pharmaceutical composition, comprising a therapeutically effective amount of the compound, or a pharmaceutically acceptable salt thereof, of claim 1, and one or more pharmaceutical excipients.

7. A method of treating a subject afflicted by a hepatocellular carcinoma associated with an altered expression of one or more kinases selected from a group consisting of b-Raf, Raf-1, and Mek1, comprising administering to the subject in need thereof a therapeutically effective amount of the compound, a pharmaceutically acceptable salt thereof, of claim 1, and one or more pharmaceutical excipients.

8. The method of claim 7, wherein the compound is independently selected from the group consisting of:

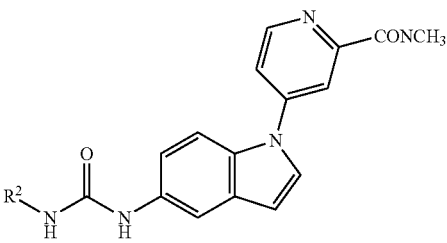

or a pharmaceutically acceptable salt thereof, and one or more pharmaceutical excipients.

9. The method of claim 7, wherein the compound is independently selected from the group consisting of:

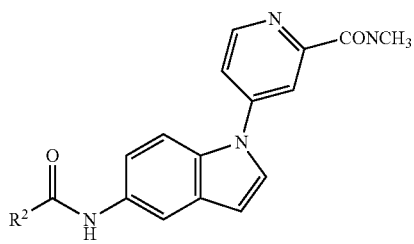

or a pharmaceutically acceptable salt thereof, and one or more pharmaceutical excipients.

10. The method of claim 7, wherein the compound is independently selected from the group consisting of:

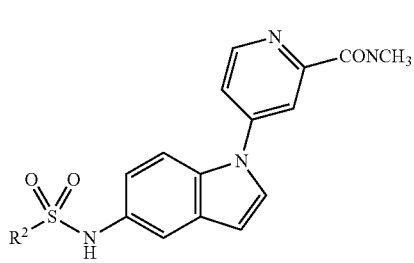

or a pharmaceutically acceptable salt thereof, and one or more pharmaceutical excipients.

11. The method of claim 7, wherein the compound is independently selected from the group consisting of:

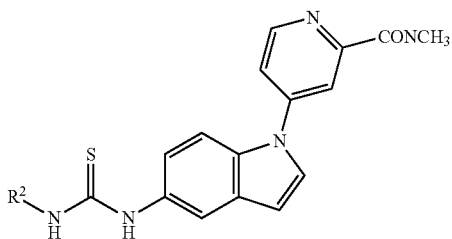

or a pharmaceutically acceptable salt thereof, and one or more pharmaceutical excipients.

12. The method of claim 7, wherein the compound is independently selected from the group consisting of:

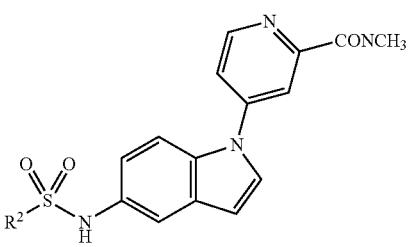

or a pharmaceutically acceptable salt thereof, and one or more pharmaceutical excipients.

13. The method of claim 7, wherein the subject is a mammal.

14. The method of claim 13, wherein the mammal is a human.

* * * * *